US008191221B2

(12) United States Patent
Suzuki et al.

(10) Patent No.: US 8,191,221 B2
(45) Date of Patent: Jun. 5, 2012

(54) LOCAL BUCKLING PERFORMANCE EVALUATING METHOD FOR STEEL PIPE, STEEL PIPE DESIGNING METHOD, STEEL PIPE MANUFACTURING METHOD, AND STEEL PIPE

(75) Inventors: Nobuhisa Suzuki, Kawasaki (JP); Katsumi Masamura, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 1277 days.

(21) Appl. No.: 11/884,749

(22) PCT Filed: Dec. 15, 2005

(86) PCT No.: PCT/JP2005/023447
§ 371 (c)(1),
(2), (4) Date: Aug. 21, 2007

(87) PCT Pub. No.: WO2007/069339
PCT Pub. Date: Jun. 21, 2007

(65) Prior Publication Data
US 2009/0208768 A1  Aug. 20, 2009

(51) Int. Cl.
*B23Q 17/00* (2006.01)
(52) U.S. Cl. ............... 29/407.05; 29/407.08; 29/407.01; 73/760; 73/787; 702/42
(58) Field of Classification Search ............... 29/407.01, 29/407.05, 407.08, 407.09; 73/760, 765, 73/786, 787, 826; 702/42
See application file for complete search history.

(56) References Cited

U.S. PATENT DOCUMENTS

| 4,384,483 A * | 5/1983 | Dellinger et al. .......... 73/152.59 |
| 5,666,287 A * | 9/1997 | Furumura et al. ............... 702/35 |
| 7,513,165 B2 * | 4/2009 | Suzuki et al. .................... 73/760 |
| 2003/0217795 A1 * | 11/2003 | Asahi et al. .................... 148/593 |
| 2008/0276714 A1 * | 11/2008 | Suzuki et al. .................... 73/760 |

FOREIGN PATENT DOCUMENTS

| EP | 1843143 A1 * | 10/2007 |
| JP | 2002-194503 A | 7/2002 |
| JP | 2005-196748 A | 7/2005 |
| JP | 2006-2893 A | 1/2006 |
| JP | 2007163392 A * | 6/2007 |
| WO | WO 2007069339 A1 * | 6/2007 |

OTHER PUBLICATIONS

Gerard, George, Compressive and Torsional Buckling of Thin-Wall Cylinders in Yield Region, NACA TN 3726, pp. 1-42 (1956).

* cited by examiner

*Primary Examiner* — Essama Omgba
(74) *Attorney, Agent, or Firm* — Young & Thompson

(57) ABSTRACT

A method for evaluating local buckling performance of a steel pipe includes obtaining a stress-strain relationship of a material having a yield plateau in the stress-strain relationship; determining the comparison of a starting strain of strain-hardening in the stress-strain relationship obtained and a critical strain of the steel pipe; and evaluating that the steel pipe has a possibility of being applied to a structure that requires plastic design when the critical strain is determined to be larger than the starting strain and evaluating that the steel pipe has no possibility of being applied to a structure that requires plastic design when the critical strain is determined to be not larger than the starting strain.

4 Claims, 14 Drawing Sheets

(a)

(b)

LOCAL BUCKLING PERFORMANCE EVALUATING METHOD FOR STEEL PIPE, STEEL PIPE DESIGNING METHOD, STEEL PIPE MANUFACTURING METHOD, AND STEEL PIPE

TECHNICAL FIELD

The present invention relates to a method for evaluating local buckling performance of steel pipes for use in gas and petroleum pipelines, etc., a method for designing steel pipes, a method for manufacturing steel pipes, and a steel pipe.

BACKGROUND ART

Construction of gas pipelines and petroleum pipelines has been promoted as the basis of energy supply. In recent years, many gas fields remote from consuming regions are developed under trends of increasing demand for natural gas. Thus, recent pipelines tend to be long and have large diameters and high pressures for large-scale transportation.

Such new pipelines use high-strength steel pipes since they are required to withstand high inner pressure despite large diameters and small pipe thickness. This is because, by reducing the pipe thickness, the cost for welding on site and cost for transporting pipes can be reduced, and the total cost of pipeline construction and operation can thus be reduced.

Although steel pipes can fully take advantages of ductility of the raw material under tensile load, local buckling occurs under compressive load since their shape of cross-section is cylindrical and has a small thickness. Whereas uniform elongation is about 10%, critical strain under compressive load is about 1 to 2%; hence, in pipeline plastic design, the critical strain is highly likely to be a controlling factor. In particular, steel pipes with small thickness tend to decrease critical strain and it is important to increase the critical strain.

Accordingly, the following proposals have been made to increase the critical strain and to thereby enhance the buckling performance.

That is, a tensile test piece taken by making the longitudinal direction of the test piece to correspond to the axial direction of a steel pipe is used to conduct tensile testing. A steel pipe having a positive nominal stress/nominal strain gradient in the observed nominal stress-nominal strain curve at any amount of strain from the yield point to 5% on-load strain amount exhibits a notably high outer diameter/pipe thickness ratio, i.e., the limit at which the local buckling occurs, when compared to a steel pipe having zero or a negative nominal stress/nominal strain gradient in the same range, and thus does not easily cause local buckling. On the basis of these findings, a steel pipe is adjusted such that the nominal stress/nominal strain gradient at any strain from the yield point to the 5% on-load strain is positive in the nominal stress/nominal strain curve observed by the tensile testing in the axial direction (refer to Patent Document 1).

Patent Document 1: Japanese Unexamined Patent Application Publication No. 9-196243

DISCLOSURE OF INVENTION

Problems to be Solved by the Invention

As described in Patent Document 1, it has been considered appropriate to use a steel material, nominal stress/nominal strain gradient of which is positive after the yielding point, in order to increase the critical strain of the steel pipe. The meaning of the phrase, "the nominal stress/nominal strain gradient is positive" is that the stress-strain curve of the steel material is of a continuous hardening type (detailed description is provided below).

This thinking has prevailed in the pipeline industries in recent years and materials not of a continuous hardening type and having a yield plateau have been considered to be unsuitable for pipeline steel pipes since such materials do not exhibit large critical strain.

The term "stress-strain curve of a continuous hardening type" means a stress-strain curve of the material in which a smooth curve is observed after the elastic region as the stress increases with the strain without showing a yield plateau (see FIG. 12).

The term "a yield-plateau-type stress-strain curve" means a curve having a yield plateau after the linear region (see FIG. 12). The elastic region in the stress-strain curve of a yield plateau type that shows a linear behavior is referred to as "linear region", a region in which the strain increases without an increase in stress is referred to as "yield plateau region", a smooth curved region after the end point of the yield plateau is referred to as "strain-hardening region", and the strain at which the strain-hardening region begins is referred to as "starting strain of strain-hardening" (see FIG. 13).

As described above, a steel pipe with a yield-plateau-type stress-strain curve (steel pipe of a yield plateau model) has been widely known to exhibit a critical strain smaller than that of a steel pipe with a continuous-hardening-type stress-strain curve. Thus, in order to obtain steel pipes with high buckling performance, such as those for construction of pipelines, the yield-plateau model steel pipes are presently automatically eliminated from the standpoint of engineering judgments.

A continuous-hardening model steel pipe is obtained by controlling the chemical composition of the steel pipe or rolling conditions of the steel sheet before pipe-making or by subjecting a steel pipe during or after pipe-making to heat treatment or processing treatment.

However, even when the continuous hardening type is maintained during the production of steel pipes, the material may undergo changes and may no longer retain the continuous hardening property by heat treatment such as that applied during coating process, for example.

In such a case, a yield plateau model is yielded, and such a steel pipe is considered to be unsuitable as steel pipes for pipelines due to its low local buckling performance according to the traditional idea.

However, it is not practical to uniformly eliminate such steel pipes. However, the only available thinking in the conventional art is to uniformly eliminate the yield plateau model; thus, it has not been possible to conceive what are the requirements needed in order for the steel pipes to be used for pipelines.

The present invention is made to overcome this problem. An object of the present invention is to provide a method for evaluating local buckling performance of a steel pipe so that it is possible to determine whether a yield plateau model can be applied to a usage that requires high local buckling performance, such as pipelines.

Another object of the present invention is to provide a method for designing a steel pipe using the technical idea used in the method for evaluating local buckling performance of the steel pipe, a method for making a steel pipe according to the designing method of the steel pipe, and a steel pipe obtained by the method for evaluating local buckling performance of the steel pipe.

Means for Solving Problems

As described above, a yield-plateau model steel pipe has low buckling performance and has been considered as unsuitable for application to pipelines that require high deformation performance.

In particular, according to a conventional method for evaluating a steel pipe shown in FIG. 14(a), whether the steel pipe is of a continuous hardening model has been the only evaluation standard, and applicability to pipelines and the like has been affirmatively evaluated when the steel pipe is of a continuous hardening model and applicability to pipelines and the like has been denied when the steel pipe is not of the continuous hardening model, i.e., when the steel pipe is of a yield plateau model.

However, if such a thinking is upheld, a steel pipe which is originally a continuous hardening model but changed to a yield plateau model by heat treatment for external coating or the like can no longer be used in pipelines.

The present inventors have questioned a conventional approach of determining local buckling performance of a steel pipe by an either- or alternative, i.e., whether the steel pipe is of a continuous hardening model or a yield plateau model. As shown in FIG. 14(b), the present inventors have conceived an idea that even a steel pipe of a yield plateau model has a possibility of being applied to pipelines etc., when the steel pipe satisfies predetermined evaluation standard and exhibits local buckling performance comparable with that of the continuous hardening model. Based on this idea, the present inventors have intensively studied what conditions a steel pipe of a yield plateau model should satisfy so that the steel pipe can exhibit local buckling performance comparable to that of the continuous hardening model, found an evaluation method therefor, and completed the present invention.

The present inventors have first studied the reason that the yield plateau model exhibits low local buckling performance.

In the cases where a steel pipe of a yield plateau model undergoes local buckling in the yield plateau region, a wrinkle develops immediately after the yield strain in the steel pipe that buckles in the yield plateau region since deformation progresses without an increase in stress in the yield plateau. Thus, the critical strain of the steel pipe that buckles in the yield plateau region is approximately the yield strain.

Thus, when buckling occurs in the yield plateau region, the critical strain is considered to be the yield strain, and the value thereof is small (about 0.1% to 0.2%). Given this, in order for a steel pipe composed of a material having a yield plateau to exhibit high buckling performance suitable for pipelines and the like, it is sufficient if the buckling point on the stress-strain curve lie after the end point of the yield plateau region (starting point of the strain-hardening region). In other words, the present inventors have found that it is sufficient if the critical strain is larger than the starting strain of strain-hardening.

Thus, the present inventors have conceived that if one can detect whether the critical strain of a particular steel pipe is larger than the starting strain of strain-hardening, then one can determine whether that steel pipe has a possibility of exhibiting high buckling performance.

Therefore, the present invention has been made.

(1) A method for evaluating local buckling performance of a steel pipe according to the present invention includes: a first step of obtaining a stress-strain relationship of a material having a yield plateau in the stress-strain relationship; a second step of determining the comparison of a starting strain of strain-hardening in the stress-strain relationship obtained in the first step and a critical strain of the steel pipe; and a third step of evaluating that the material has a possibility of being applied to a structure that requires plastic design when the critical strain is determined to be larger than the starting strain of strain-hardening in the second step and evaluating that the material has no possibility of being applied to a structure that requires plastic design when the critical strain is determined to be not larger than the starting strain of strain-hardening in the second step.

The first step is a step of obtaining a stress-strain relationship of a steel material having a yield plateau. The term "stress-strain relationship" here refers to point-sequence data indicating the relationship between the stress and the strain when the steel material is subjected to tensile testing or a stress-strain curve or the like based on such data, for example. One example of the stress-strain curve obtained is shown in FIG. 15.

The second step is a step of determining the comparison of the starting strain of strain-hardening in the stress-strain relationship obtained in the first step and the critical strain of a steel pipe composed of the material. There is no need to determine the critical strain of the steel pipe; and only the comparison of the starting strain of strain-hardening and the critical strain should be determined. Thus, for example, an experimental steel pipe may be produced and tested whether it undergoes buckling under a load that would cause a strain corresponding to the starting strain of strain-hardening so that the starting strain of strain-hardening can be determined to be larger if the experimental steel pipe undergoes buckling.

In the third step, the material is evaluated as having a possibility of being applied to a structure that requires plastic design when the critical strain is determined to be larger than the starting strain of strain-hardening in the second step and evaluated as having no possibility of being applied to a structure that requires plastic design when the critical strain is determined to be not larger than the starting strain of strain-hardening in the second step.

A structure that requires plastic design is, in other words, a structure that requires high deformation performance (critical strain). An example thereof is pipelines.

According to the method in (1) above, application of the steel pipe can be determined by simply determining the comparison of the starting strain of strain-hardening and the critical strain of the steel pipe composed of that material. Thus, the method is particularly convenient.

In the method of (1) above, no particular limit is imposed on the method for determining the comparison of the starting strain of strain-hardening and the critical strain of the steel pipe composed of the material. However, it takes time and cost if an experimental steel pipe is used as described in (1). Therefore, the following is provided:

(2) According to a method for evaluating local buckling performance of a steel pipe of the present invention, in the second step of the method of (1) above for determining the comparison of the starting strain of strain-hardening and the critical strain of the steel pipe composed of the material, when the critical strain can be calculated by inputting the stress-strain relationship obtained in the first step to equation below, the critical strain is determined to be larger than the starting strain of strain-hardening, and when the critical strain cannot be calculated, the critical strain is determined to be not larger than the starting strain of strain-hardening:

$$\varepsilon_{cr} = \frac{4}{3}\sqrt{\frac{E_{Tcr}}{E_{Scr}}} \frac{t}{D} \quad (1.1)$$

wherein $\epsilon_{cr}$: compressive critical strain $E_{Scr}$: inclination of a line connecting the origin and the buckling point in the yield-plateau-model stress-strain curve $E_{Tcr}$: inclination of the stress-strain curve at the buckling point t: pipe thickness D: pipe diameter First, Equation (1.1) above is described.

The fundamental equation expressing the local bucking strain of a steel pipe under compressive force is Equation (1.2) below:

$$\varepsilon_{cr} = \frac{2}{\sqrt{3(1-v^2)}}\sqrt{\frac{E_{Tcr}}{E_{Scr}}} \frac{t}{D} \quad (1.2)$$

In Equation (1.2), $\epsilon_{cr}$ represents a compressive critical strain, v represents a Poisson's ratio, t represents a pipe thickness, and D represents a pipe diameter. $E_{Scr}$ represents an inclination (referred to as "secant modulus" hereinafter) of line connecting the origin and the buckling point in the yield-plateau-model stress-strain curve shown in FIG. 15, and $E_{Tcr}$ represents an inclination (referred to as "tangent modulus" hereinafter) of the stress-strain curve at the buckling point. In the graph, $\epsilon_H$ represents a starting strain of strain-hardening. However, in FIG. 15, the stress-strain curve in the strain-hardening region is depicted as a curve to express an arbitrary relationship.

By substituting 0.5 as the Poisson's ratio v of Equation (1.2) in the case of plastic deformation, Equation (1.1) above can be obtained.

Next, the method for determining whether the critical strain of a particular steel pipe is larger than the starting strain of strain-hardening using Equation (1.1) is described.

As is apparent from Equation (1.1), the critical strain is expressed as a function of the shape of the stress-strain curve and (t/D). Equation (1.1) means that the value of the left-hand side of the equation is the critical strain if the equality is true. Thus, if substitution of the secant modulus ($E_S$) and the tangent modulus ($E_T$) in the fundamental equation at a point on the stress-strain curve at a particular strain renders the equality to be true, then that strain is the critical strain. Since the tangent modulus is zero in the yield plateau region, the right-hand side of Equation (1.1) is incomputable. Accordingly, the fact that the critical strain is computable at least indicates that the critical strain is larger than the starting strain of strain-hardening.

Whether the critical strain is computable can be determined by whether Equation (1.1) proves to be true by trial-and-error computation involving substitution of a strain not less than the starting strain of strain-hardening obtained by the stress-strain relationship obtained in the first step.

However, it is onerous to repeat trial-and-error computation by substitution of strain values in Equation (1.1). Thus, a method for determining whether the critical strain is larger than the starting strain of strain-hardening without repetitive trial-and-error computation is described next.

(3) According to another method for evaluating local buckling performance of the steel pipe according to the present invention, in the method described in (1), the determination of the comparison of the starting strain of strain-hardening and the critical strain of the steel pipe composed of the material in the second step is conducted on the basis of an equation below and the stress-strain relationship obtained in the first step, and the right-hand side of the equation below corresponding to the starting strain of strain-hardening is computed, and when the computed value is larger than the starting strain of strain-hardening, the critical strain is determined to be larger than the starting strain of strain-hardening, and when the computed value is not more than the starting strain of strain-hardening, the critical strain is evaluated as not larger than the starting strain of strain-hardening:

$$\varepsilon_{cr} = \frac{4}{3}\sqrt{\frac{E_{Tcr}}{E_{Scr}}} \frac{t}{D} \quad (1.1)$$

wherein $\epsilon_{cr}$: compressive critical strain $E_{Scr}$: inclination of a line connecting the origin and the buckling point in the yield-plateau-model stress-strain curve $E_{Tcr}$: inclination of the stress-strain curve at the buckling point t: pipe thickness D: pipe diameter The method of (3) above will now be described.

The secant modulus ($E_S$) and the tangent modulus ($E_T$) are determined for a point on the stress-strain curve corresponding to a strain (assumed strain) of the abscissa shown in FIG. 15 and substituted in Equation (1.1) to calculate the value of the right-hand side. The calculated values are plotted with the ordinate indicating the calculated values and the abscissa indicating the assumed strain, giving a graph shown in FIG. 1.

As shown in FIG. 1, since the stress-strain curve passing through the origin is substantially linear up to the yield strain, the calculated values are constant. In the yield plateau region, since the tangent modulus is zero, the calculated strain is zero at any point. In the strain-hardening region, the calculated strain shows a monotonic decrease.

Equation (1.1) means that the value at the left-hand side is the critical strain when the equality is true. According to FIG. 1, the equality is true on the 1:1 line.

Therefore, the strain corresponding to the intersection with the 1:1 line in FIG. 1 is the critical strain.

Thus, determination of whether the critical strain is larger than the starting strain of strain-hardening should be conducted by comparing this strain and the starting strain of strain-hardening.

However, in order to determine whether the critical strain is larger than the starting strain of strain-hardening, it is not always necessary to determine the critical strain.

The cases where the critical strain is larger than the starting strain of strain-hardening are cases where the decreasing curve intersects with the 1:1 line in FIG. 1, for example. In order for the 1:1 line to intersect with the decreasing curve, the calculated value corresponding to the starting strain of strain-hardening must be larger than the starting strain of strain-hardening (refer to encircled numeral 2 in FIG. 1).

On the contrary, the cases where the critical strain is not larger than the starting strain of strain-hardening are cases where the decreasing curve has no intersection with the 1:1 curve (refer to encircled numeral 1 in FIG. 1). In such cases, the calculated value corresponding to the starting strain of strain-hardening is not larger than the starting strain of strain-hardening.

Accordingly, in order to determine whether the critical strain is larger than the starting strain of strain-hardening, the calculated value corresponding to the starting strain of strain-hardening should be compared with the starting strain of strain-hardening.

Thus, in the present invention, the right-hand side of Equation (1.1) is calculated for a point on the stress-strain curve corresponding to the starting strain of strain-hardening, and the resulting calculated value is compared with the starting strain of strain-hardening. If the calculated value is larger, then the critical strain is determined to be larger than the starting strain of strain-hardening.

According to this method, however, it is still necessary to calculate the secant modulus ($E_S$) and the tangent modulus ($E_T$) at a point on the stress-strain relationship corresponding to the starting strain of strain-hardening in order to calculate the right-hand side of Equation (1.1). Thus, complex computation is necessary. Thus, in order to simplify the computation, the following is provided:

(4) According to another method of evaluating local buckling performance of the steel pipe of the present invention, determination of the comparison of the starting strain of strain-hardening and the critical strain of the steel pipe composed of the material in the second step is performed on the basis of Equation (2.1) below instead of Equation (1.1):

$$\varepsilon_{cr} = \frac{16}{9(\varepsilon_y/m - \varepsilon_H)}\left(\frac{t}{D}\right)^2 \qquad (2.1)$$

wherein D/t: maximum pipe diameter/pipe thickness ratio
$\epsilon_y$: yield strain
$\epsilon_H$: starting strain of strain-hardening
m: modulus of strain-hardening Equation (2.1) is described below. The relationship between the stress and the strain in the strain-hardening region of the stress-strain curve shown in FIG. 15 can be rewritten as a straight line having an inclination of mE shown in FIG. 2. The relationship between the stress and strain, the tangent modulus $E_T$, and the secant modulus $E_S$ in the strain-hardening region are expressed by the following equations:

$$\sigma = \sigma_y + mE(\varepsilon - \varepsilon_H) \qquad (2.2)$$
$$E_T = \frac{d\sigma}{d\varepsilon} = mE \qquad (2.3)$$
$$E_S = \frac{\sigma}{\varepsilon} = \frac{\sigma_y + mE(\varepsilon - \varepsilon_H)}{\varepsilon} \qquad (2.4)$$

Thus, $E_T/E_S$ can be determined by the following equation:

$$\frac{E_T}{E_S} = \frac{mE\varepsilon}{\sigma_y + mE(\varepsilon - \varepsilon_H)} = \frac{1}{1 + (\varepsilon_y/m - \varepsilon_H)/\varepsilon} \qquad (2.5)$$

If the strain in Equation (2.5) is expressed as the critical strain and substituted in Equation (1.1), then the following equation can be yielded:

$$\varepsilon_{cr} = \frac{4}{3}\sqrt{\frac{E_T}{E_S}}\frac{t}{D} = \frac{4}{3}\sqrt{\frac{1}{1+\xi/\varepsilon_{cr}}}\frac{t}{D} \qquad (2.6)$$

where $\zeta = \epsilon_y/m - \epsilon_H$.

If Equation (2.6) is solved for the critical strain, then the compressive critical strain of the steel pipe in the strain-hardening region can be expressed by Equation (2.7):

$$\varepsilon_{cr} = -\frac{\xi}{2} + \sqrt{\left(\frac{\xi}{2}\right)^2 + \frac{16}{9}\left(\frac{t}{D}\right)^2} \qquad (2.7)$$

If Equation (2.7) is transformed into Equation (2.8) below and the second term of the right-hand side of Equation (2.8) is subjected to linear approximation, then the critical strain is expressed by Equation (2.9), which is Equation (2.1) described above:

$$\varepsilon_{cr} = -\frac{\xi}{2} + \frac{\xi}{2}\sqrt{1 + \left(\frac{2}{\xi}\right)^2\frac{16}{9}\left(\frac{t}{D}\right)^2} \qquad (2.8)$$

$$\varepsilon_{cr} = -\frac{\xi}{2} + \frac{\xi}{2}\left\{1 + \frac{1}{2}\left(\frac{2}{\xi}\right)^2\frac{16}{9}\left(\frac{t}{D}\right)^2\right\} \qquad (2.9)$$
$$= \frac{16}{9\xi}\left(\frac{t}{D}\right)^2$$
$$= \frac{16}{9(\varepsilon_y/m - \varepsilon_H)}\left(\frac{t}{D}\right)^2$$

(5) According to another method for evaluating local buckling performance of the steel pipe according to the present invention, the determination of comparison of the starting strain of strain-hardening and the critical strain of the steel pipe using the material in the second step of (3) above is conducted on the basis of Equation (3.1) below instead of Equation (1.1):

$$\varepsilon_{cr} = \frac{4}{3}\sqrt{1 - \frac{c}{\sigma_y}}\sqrt{b}\frac{t}{D} \qquad (3.1)$$

wherein D/t: maximum pipe diameter/pipe thickness ratio
$\sigma_y$: yield stress
c: regression coefficient of Dower-law function
b: regression coefficient of power-law function Equation (3.1) above will now be described.

The relationship between the stress and the strain in the strain-hardening region in the stress-strain curve shown in FIG. 15 approximated by a power-law function is shown in FIG. 3. The relationship between the stress and the strain, the tangent modulus $E_T$, and the secant modulus $E_S$ in the strain-hardening region are expressed by the following equations:

$$\sigma = a\varepsilon^b + c \qquad (3.2)$$

wherein a, b, and c are each a regression coefficient of power-law function, $$E_T = \frac{d\sigma}{d\varepsilon} = ab\varepsilon^{b-1} \qquad (3.3)$$
$$E_S = \frac{\sigma}{\varepsilon} = \frac{a\varepsilon^b + c}{\varepsilon} \qquad (3.4)$$

Thus, the ratio of the tangent modulus to the secant modulus is expressed by the following equation:

$$\frac{E_T}{E_S} = \frac{ab\varepsilon^{b-1}}{(a\varepsilon^b_{cr} + c)/\varepsilon} = \frac{ab\varepsilon^b}{a\varepsilon^b + c} = \frac{b}{1 + c/a\varepsilon^b} \qquad (3.5)$$

The strain in Equation (3.5) expressed as the critical strain is substituted in Equation (1.1) to give the following equation:

$$\varepsilon_{cr} = \frac{4}{3}\sqrt{\frac{E_{Tcr}}{E_{Scr}}}\frac{t}{D} = \frac{4}{3}\sqrt{\frac{b}{1+c/a\varepsilon_{cr}^b}}\frac{t}{D} \qquad (3.6)$$

This equation can be rewritten for compressive critical strain of the steel pipe as Equation (3.7):

$$\varepsilon_{cr} = \frac{4}{3}\sqrt{\frac{b}{1+c/a\varepsilon_{cr}^b}}\frac{t}{D} \qquad (3.7)$$

$$= \frac{4}{3}\sqrt{\frac{b}{1+c/(\sigma_{cr}-c)}}\frac{t}{D}$$

$$= \frac{4}{3}\sqrt{\frac{b}{\sigma_{cr}/(\sigma_{cr}-c)}}\frac{t}{D}$$

$$\varepsilon_{cr} = \frac{4}{3}\sqrt{\frac{b}{\sigma_{cr}/(\sigma_{cr}-c)}}\frac{t}{D}$$

$$= \frac{4}{3}\sqrt{\left(1-\frac{c}{\sigma_{cr}}\right)b}\frac{t}{D}$$

However, since the critical stress is included in the right-hand side of Equation (3.7), the compressive critical strain cannot be determined as it is.

Thus, in order to solve Equation (3.7), the property that the critical stress is close to the yield stress is utilized as show in Equation (3.8). Accordingly, the compressive critical strain of the steel pipe is expressed by Equation (3.9), which is Equation (3.1) described above:

$$\sigma_{cr} \approx \sigma_y \qquad (3.8)$$

$$\varepsilon_{cr} = \frac{4}{3}\sqrt{\left(1-\frac{c}{\sigma_{cr}}\right)b}\frac{t}{D} = \frac{4}{3}\sqrt{\left(1-\frac{c}{\sigma_y}\right)b}\frac{t}{D} \qquad (3.9)$$

(6) Another method for evaluating local buckling performance of the steel pipe of the present invention includes a fourth step of determining the critical strain and a fifth step of comparing, in cases where the possibility of application is affirmed in the third step in (1) to (5) above, compare the critical strain determined in the fourth step with a required critical strain required for the application and determining possibility of the application in the fifth step.

Any one of the methods described in (2) in which Equation (1.1) is used, (4) in which Equation (2.1) is used, and (5) in which Equation (3.1) is used can be used as the method for determining the critical strain in the fourth step.

It should be noted that "required critical strain" refers to a strain required for the steel pipe at the time when the steel pipe undergoes local buckling during use.

(7) A method for evaluating local buckling performance of a steel pipe according to the present invention includes a first step of obtaining a stress-strain relationship of a material having a yield plateau in the stress-strain relationship; a second step of inputting the stress-strain relationship obtained in the first step to an equation below to conduct computation for determining a critical strain; and a third step of evaluating that the steel pipe has a possibility of being applied to a structure that requires plastic design when the critical strain is determined in the second step and that the steel pipe has no possibility of being applied to a structure that requires plastic design when the critical strain is incomputable in the second step:

$$\varepsilon_{cr} = \frac{4}{3}\sqrt{\frac{E_{Tcr}}{E_{Scr}}}\frac{t}{D} \qquad (1.1)$$

wherein $\varepsilon_{cr}$: compressive critical strain $E_{Scr}$: inclination of a line connecting the origin and the buckling point in the yield-plateau-model stress-strain curve $E_{Tcr}$: inclination of the stress-strain curve at the buckling point t: pipe thickness D: pipe diameter (8) A method for evaluating local buckling performance of a steel pipe of the present invention includes: a first step of obtaining a stress-strain relationship of a material having a yield plateau in the stress-strain relationship; a second step of inputting the stress-strain relationship obtained in the first step to an equation below to conduct computation for determining a critical strain; and a third step of evaluating that the steel pipe has no possibility of being applied to a structure that requires plastic design when the critical strain is incomputable in the second step and, when the critical strain is computed in the second step, comparing the computed critical strain with a required critical strain required for the application so as to determine the possibility of the application:

$$\varepsilon_{cr} = \frac{4}{3}\sqrt{\frac{E_{Tcr}}{E_{Scr}}}\frac{t}{D} \qquad (1.1)$$

wherein $\varepsilon_{cr}$: compressive critical strain $E_{Scr}$: inclination of line connecting the origin and the buckling point in the yield-plateau-model stress-strain curve $E_{TCr}$: inclination of the stress-strain curve at the buckling point t: pipe thickness D: pipe diameter In the inventions described in (1) to (8) above, the buckling performance of the steel pipe is determined on the basis of whether the critical strain of the steel pipe is larger than the starting strain of strain-hardening or whether the critical strain is computable.

Methods for evaluating buckling performance of the steel pipe on the basis of the diameter/pipe thickness ratio (D/t) of the steel pipe are described below.

The relationship between the local buckling $\varepsilon_{cr}$ and the pipe diameter/pipe thickness ratio (D/t) of the steel pipe is expressed by Equation (1.1) described above. Equation (1.1) is plotted with the pipe diameter/pipe thickness ratio (D/t) in the abscissa and the critical strain $\varepsilon_{cr}$ in the ordinate to give a graph shown in FIG. 4.

As is apparent from FIG. 4, when the D/t of the steel pipe is small (thick walled steel pipe), the critical strain $\varepsilon_{cr}$ is large. Increasing D/t of the steel pipe, i.e., decreasing the thickness of the steel pipe, decreases the critical strain $\varepsilon_{cr}$. At a point where the critical strain $\varepsilon_{cr}$ becomes the same as the starting strain of strain-hardening, the critical strain drastically decreases, and the critical strain $\varepsilon_{cr}$ thereafter becomes the same as the yield strain.

Therefore, by determining the pipe diameter/pipe thickness ratio $(D/t)_{cr}$ at which the critical strain $\varepsilon_{cr}$ becomes the same as the starting strain of strain-hardening, it becomes possible to determine whether the steel pipe undergoes buckling in the yield plateau region or in the strain-hardening region or whether the steel pipe has good buckling performance by comparing the pipe diameter/pipe thickness ratio (D/t)$_{cr}$ and the pipe diameter/pipe thickness ratio (D/t) of the steel pipe to be evaluated. In this respect, the following is provided.

(9) A method for evaluating local buckling performance of a steel pipe of the present invention includes: a first step of obtaining a stress-strain relationship of a steel material having a yield plateau; a second step of determining a pipe diameter/pipe thickness ratio (D/t)$_{cr}$ at which a critical strain of the steel pipe having the stress-strain relationship becomes the same as a starting strain of strain-hardening in the stress-strain relationship; and a third step of comparing the comparison of a pipe diameter/pipe thickness ratio (D/t) of a steel pipe to be evaluated and the pipe diameter/pipe thickness ratio (D/t)$_{cr}$ determined in the second step and evaluating that the material has a possibility of being applied to a structure that requires plastic design when the pipe diameter/pipe thickness ratio (D/t) of the steel pipe to be evaluated is smaller and that the material has no possibility of being applied to a structure that requires plastic design when the pipe diameter/pipe thickness ratio (D/t) of the steel pipe to be evaluated is larger.

The method for determining the pipe diameter/pipe thickness ratio (D/t)$_{cr}$ in the second step is not particularly limited. One example thereof is a method that uses Equation (1.1) below, which is previously described:

$$\varepsilon_{cr} = \frac{4}{3}\sqrt{\frac{E_{Tcr}}{E_{Scr}}}\frac{t}{D} \quad (1.1)$$

Equation (1.1) means that when the equality is true, the value of the left-hand side is the critical strain. Thus, in order for the steel pipe to undergo buckling at a starting strain of strain-hardening in the stress-strain relationship obtained in the first step, the starting strain of strain-hardening should be substituted in the left-hand side of Equation (1.1), the secant modulus (E$_S$) and the tangent modulus (E$_T$) at a point on the stress-strain relationship corresponding to the starting strain of strain-hardening should be determined, and these values should be substituted in the right-hand side of Equation (1.1) to determine the pipe diameter/pipe thickness ratio (D/t) at which the equality is true.

According to this method, however, it is still necessary to calculate the secant modulus (E$_S$) and the tangent modulus (E$_T$) at a point on the stress-strain relationship corresponding to the starting strain of strain-hardening in order to calculate the right-hand side of Equation (1.1). Thus, complex computation is necessary. Thus, in order to further simplify the computation, the following is provided:

(10) According to another method of evaluating local buckling performance of the steel pipe of the present invention, in the second step of (9) above, the pipe diameter/pipe thickness ratio (D/t)$_{cr}$ is determined on the basis of Equation (4.1) below and the stress-strain relationship obtained in the first step in (9) above:

$$\left(\frac{D}{t}\right)_{cr} = \frac{4}{3\sqrt{(\varepsilon_y/m - \varepsilon_H)\varepsilon_H}} \quad (4.1)$$

wherein D/t: maximum pipe diameter/pipe thickness ratio
$\varepsilon_y$: yield strain
$\varepsilon_H$: starting strain of strain-hardening
m: modulus of strain-hardening Equation (4.1) is obtained by solving Equation (2.1) for the pipe diameter/pipe thickness ratio (D/t)$_{cr}$ while substituting the critical strain $\varepsilon_{cr}$ with the starting strain or strain-hardening $\varepsilon_H$ to determine the pipe diameter/pipe thickness ratio (D/t)$_{cr}$ at which the critical strain becomes the same as the starting strain of strain-hardening in the stress-strain relationship.

(11) Another method for evaluating the local buckling performance of the steel pipe of the present invention is characterized in that, in the second step of (9) above, the maximum pipe diameter/pipe thickness ratio (D/t)$_{cr}$ is determined on the basis of Equation (5.1) and the stress-strain relationship obtained in the first step of (9) above:

$$\left(\frac{D}{t}\right)_{cr} = \frac{4}{3\varepsilon_H}\sqrt{\left(1 - \frac{c}{\sigma_y}\right)b} \quad (5.1)$$

wherein D/t: maximum pipe diameter/pipe thickness ratio
$\varepsilon_y$: yield strain
$\varepsilon_H$: starting strain of strain-hardening
m: modulus of strain-hardening Equation (5.1) is obtained by solving equation (3.1) for the pipe diameter/pipe thickness ratio (D/t)$_{cr}$ while substituting the critical strain $\varepsilon_{cr}$ with the starting strain of strain-hardening $\varepsilon_H$ to determine the pipe diameter/pipe thickness ratio (D/t)$_{cr}$ at which the critical strain becomes the same as the starting strain of strain-hardening in the stress-strain relationship.

(12) Another method for evaluating local buckling performance of a steel pipe is the method according to any one of (9) to (11) above, including a fourth step of determining a critical strain and a fifth step of comparing the critical strain determined in the fourth step with a required critical strain required for the application when the possibility of application is affirmatively determined in the third step so as to determine the possibility of the application.

Any one of the methods described in (2) in which Equation (1.1) is used, (4) in which Equation (2.1) is used, and (5) in which Equation (3.1) is used can be used as the method for determining the critical strain in the fourth step.

(13) A method for designing a steel pipe of the present invention includes: a first step of obtaining a stress-strain relationship of a steel material having a yield plateau; a second step of determining a pipe diameter/pipe thickness ratio (D/t)$_{cr}$ at which a critical strain of the steel pipe having the stress-strain relationship becomes the same as a starting strain of strain-hardening in the stress-strain relationship; and a third step of determining a pipe diameter/pipe thickness ratio (D/t) of a steel pipe to be evaluated while maintaining the pipe diameter/pipe thickness ratio (D/t) of the steel pipe to be evaluated to be smaller than the maximum pipe diameter/pipe thickness ratio (D/t)$_{cr}$ determined in the second step.

(14) According to a method for designing a steel pipe of the present invention, in the third step in (13) above, the pipe diameter/pipe thickness ratio (D/t) of the steel pipe to be designed is determined such that a critical strain determined from the stress-strain relationship obtained in the first step and the pipe diameter/pipe thickness ratio (D/t) of the steel pipe to be evaluated is larger than a required critical strain.

(15) A method for producing a steel pipe of the present invention is characterized in that the steel pipe is produced on the basis of design according to the method for designing the steel pipe described in (13) or (14) above.

(16) A method for evaluating local buckling performance of a steel pipe of the present invention is a method for evaluating local buckling performance of a steel pipe, pipe diameter D, pipe thickness t, and required critical strain $\varepsilon_{req}$ of which are given, characterized in obtaining a stress-strain relationship of a material having a yield plateau in the stress-strain relationship; determining whether the yield strain $\epsilon_y$, the modulus of strain-hardening m, and the starting strain of strain-hardening $\epsilon_H$ of a stress-strain curve of the stress-strain relationship obtained are in a region defined by equations below in a coordinate plane with an ordinate indicating $\epsilon_y/m$ and an abscissa indicating $\epsilon_H$; and evaluating that the steel pipe has a possibility of being applied to a structure that requires plastic design when these values are within the region and that the steel pipe has no possibility of being applied to structures that require plastic design when these values are outside the region:

$$\left\{\varepsilon_H + \frac{4}{3}\left(\frac{t}{D}\right)\right\} \le \frac{\varepsilon_y}{m} \le \left\{\varepsilon_H + \frac{16}{9\varepsilon_{req}}\left(\frac{t}{D}\right)^2\right\} \quad (30)$$
wherein $\varepsilon_y \le \varepsilon_H \le \varepsilon_{req}$ and $$\left\{\varepsilon_H + \frac{4}{3}\left(\frac{t}{D}\right)\right\} \le \frac{\varepsilon_y}{m} \le \left\{\varepsilon_H + \frac{16}{9\varepsilon_H}\left(\frac{t}{D}\right)^2\right\} \quad (31)$$
wherein $\varepsilon_{req} < \varepsilon_H < \frac{4}{3}\left(\frac{t}{D}\right)$.

Equations (30) and (31) will now be described.

The relationship between the compressive critical strain $\epsilon_{cr}$ and the pipe diameter/pipe thickness ratio (D/t) of the steel pipe is indicated by Equation (1.1) previously described. Equation (1.1) plotted with the abscissa indicating the pipe diameter/pipe thickness ratio (D/t) and the ordinate indicating the compressive critical strain $\epsilon_{cr}$ gives a graph shown in FIG. 4.

As is apparent from FIG. 4, when the D/t of the steel pipe is small (thick walled steel pipe), the compressive critical strain $\epsilon_{cr}$ is large. Increasing D/t of the steel pipe, i.e., decreasing the thickness of the steel pipe, decreases the compressive critical strain $\epsilon_{cr}$. At a point where the compressive critical strain $\epsilon_{cr}$ becomes the same as the starting strain of strain-hardening, the compressive critical strain $\epsilon_{cr}$ drastically decreases, and the compressive critical strain $\epsilon_{cr}$ thereafter becomes substantially the same as the yield strain $\epsilon_y$.

FIG. 4 shows that the reason that the buckling performance of the yield-plateau model steel pipe is low is the drastic decrease in compressive critical strain at the point where the compressive critical strain $\epsilon_{cr}$ becomes the same as the starting strain of strain-hardening $\epsilon_H$. This is because, in the yield plateau region, since deformation progresses without a decrease in stress, the steel pipe that undergoes buckling in the yield plateau region allows the buckling mode to develop immediately after the yield strain. Thus, the compressive critical strain is approximately the yield strain.

As discussed above, one reason for low deformation performance of a yield-plateau model steel pipe is that the compressive critical strain of a steel pipe that undergoes buckling in the yield plateau region is approximately a yield strain. This indicates that the value of the starting strain of strain-hardening $\epsilon_H$ on the stress-strain curve of the yield-plateau model steel pipe, i.e., the length of the yield plateau, is involved in the deformation performance of the steel pipe.

In other words, it can be conceived that a steel pipe having a small starting strain of strain-hardening $\epsilon_H$, i.e., a short yield plateau, exhibits deformation performance superior to that of a steel pipe having a large starting strain of strain-hardening $\epsilon_H$, i.e., a long yield plateau.

Therefore, it is effective to use the value of the starting strain of strain-hardening $\epsilon_H$ as the index for evaluating the deformation performance of yield-plateau model steel pipes.

The present inventors have further investigated the index for evaluating deformation performance other than the length of the yield plateau.

The present inventors have paid attention to the fact that, according to Equation (1.1), the compressive critical strain $\epsilon_{cr}$ increases with $E_{Tcr}/E_{Scr}$. As is apparent from FIG. 15, the present inventors have found that since $E_{Tcr}$ is an inclination in the stress-strain curve, a large inclination of the stress-strain curve near the end point of the yield plateau causes the compressive critical strain $\epsilon_{cr}$ to be large.

Based on this finding, the present inventors have found that it is effective to use the inclination of the stress-strain curve as the index for evaluating the deformation performance of yield-plateau model steel pipes.

In view of the above, by observing the shape of the stress-strain curve, evaluation of deformation performance becomes possible. The "shape of stress-strain curve" monitored here means the length of the yield plateau and the magnitude of the tangential gradient in the strain-hardening region.

The description above is a schematic explanation on the basis of Equation (1.1) that the deformation performance of a steel pipe can be evaluated by the shape of the stress-strain curve.

The preset inventors have further investigated for a mathematical equation indicating the compressive critical strain of the yield plateau model by rewriting the fundamental equation described above to conceive a quantitative evaluation method that uses mathematical equations on the basis of the above findings.

This point will now be described in detail.

As described above, the compressive critical strain $\epsilon_{cr}$ of a yield-plateau model steel pipe can be expressed by Mathematical Equation (11) below (the same equation as Equation (2.1) above):

$$\varepsilon_{cr} = \frac{16}{9(\varepsilon_y/m - \varepsilon_H)}\left(\frac{t}{D}\right)^2 \quad (11)$$

wherein D/t: pipe diameter/pipe thickness ratio
$\epsilon_y$: yield strain
$\epsilon_H$: starting strain of strain-hardening
m: modulus of strain-hardening As described above and shown in Equation (11), the compressive critical strain $\epsilon_{cr}$ of a yield-plateau model steel pipe can be expressed by the modulus of strain-hardening m indicating the inclination of the stress-strain curve and the starting strain of strain-hardening $\epsilon_H$ used as the index of the length of the yield plateau. In the description below, a method for evaluating the local buckling performance of the steel pipe that uses Equation (11) is specifically described.

Note that the application range of Equation (11) that assumes the compressive critical strain of a yield plateau model can be expressed for the pipe diameter/pipe thickness ratio (D/t) by the following equation by assuming the compressive critical strain and the starting strain of strain-hardening to be equal. That is, provided that the characteristics of a stress-strain curve of a yield-plateau model are given, the maximum pipe diameter/pipe thickness ratio $(D/t)_{max}$ of the applicable steel pipe is expressed by Equation (12). Thus, Equation (11), which is the equation for assuming the critical strain, cannot be applied to a steel pipe having D/t larger than the $(D/t)_{max}$.

$$\left(\frac{D}{t}\right)_{max} = \frac{4}{3}\frac{1}{\sqrt{(\varepsilon_y/m - \varepsilon_H)\varepsilon_H}} \quad (12)$$

When the pipe diameter D, the pipe thickness t, and the required critical strain $\epsilon_{req}$ are given, the following requirements must be met in order for a steel pipe produced from a yield-plateau model material to satisfy the required critical strain $\epsilon_{req}$ and be applicable to steel pipes for pipelines:

(A) The compressive critical strain $\epsilon_{cr}$ of the steel pipe is larger than the required critical strain $\epsilon_{req}$.

(B) The steel pipe does not undergo local buckling in the yield plateau region, i.e., local buckling of the steel pipe occurs in the strain-hardening region.

(C) The starting strain of strain-hardening is larger than the yield strain.

In other words, the steel pipe can be evaluated as being applicable to pipeline steel pipes if the steel pipe satisfy all of the requirements (A) to (C) and can be evaluated as being inapplicable to pipeline steel pipes if the steel pipe fails to satisfy any one of the requirements (A) to (C).

FIG. 16 shows the above three conditions as regions in a coordinate plane with the ordinate indicating $\epsilon_y$ and the abscissa indicating $\epsilon_H$.

In the description below, the reasons that necessitate the three requirements are described, and FIG. 16 showing these conditions in a diagram is explained.

(A) Condition that the compressive critical strain $\epsilon_{cr}$ of the steel pipe is larger than the required critical strain $\epsilon_{req}$ In actual designing of steel pipes for pipelines, the required value of critical strain (required critical strain $\epsilon_{req}$) is given.

Therefore, in order for the steel pipe to be applicable to a steel pipe for pipelines, it is a necessary condition that the compressive critical strain $\epsilon_{cr}$ of the steel pipe be larger than the required critical strain $\epsilon_{req}$. That is, in evaluating whether the steel pipe is applicable to a steel pipe for pipelines, whether the compressive critical strain $\epsilon_{cr}$ of the steel pipe is larger than the required critical strain $\epsilon_{req}$ must be determined.

That the compressive critical strain $\epsilon_{cr}$ is larger than the value of the required critical strain $\epsilon_{req}$ can be expressed by Equation (13) below from Equation (11):

$$\varepsilon_{req} \le \varepsilon_{cr} = \frac{16}{9(\varepsilon_y/m - \varepsilon_H)}\left(\frac{t}{D}\right)^2 \tag{13}$$

Equation (14) can be obtained by rewriting Equation (13) for $\epsilon_y/m$. $\epsilon_y/m$ and $\epsilon_H$ that satisfy the inequality sign of Equation (13) form the region on and below a straight line (a) in FIG. 16. The straight line (a) is expressed by Equation (15) obtained by substituting the inequality sign of Equation (14) with an equality sign. For combinations of $\epsilon_y/m$ and $\epsilon_H$ on the straight line (a), $\epsilon_{cr}$ and $\epsilon_{req}$ are equal.

$$\frac{\varepsilon_y}{m} \le \left\{\varepsilon_H + \frac{16}{9\varepsilon_{req}}\left(\frac{t}{D}\right)^2\right\} \tag{14}$$

$$\frac{\varepsilon_y}{m} = \left\{\varepsilon_H + \frac{16}{9\varepsilon_{req}}\left(\frac{t}{D}\right)^2\right\} \tag{15}$$

For safety considerations, since $\epsilon_{cr}$ is required to be larger than $\epsilon_{req}$, $\epsilon_y/m$ and $\epsilon_H$ selected are values on a straight line extending parallel to and below the straight line (a). In other words, by selecting a combination of $\epsilon_y/m$ and $\epsilon_H$ on a straight line extending parallel to and below the straight line (a), $\epsilon_{cr}$ becomes larger than $\epsilon_{req}$.

However, $\epsilon_{req}$ cannot exceed the maximum value of $\epsilon_{req}$ (maximum compressive critical strain $\epsilon_{crmax}$). Thus, a limit value exists for the line parallel to and below the straight line (a). The limit value will be described below.

(B) Condition that the steel pipe does not undergo local buckling in the yield plateau region, i.e., local buckling of the steel pipe occurs in the strain-hardening region In order for a steel pipe to undergo local buckling in the strain-hardening region, it is a necessary condition that the compressive critical strain $\epsilon_{cr}$ be larger than the starting strain of strain-hardening $\epsilon_H$. This condition can be expressed by Equation (16) below by substituting the required critical strain $\epsilon_{req}$ left-hand side of Equation (13) with the starting strain of strain-hardening $\epsilon_H$:

$$\varepsilon_H \le \frac{16}{9(\varepsilon_y/m - \varepsilon_H)}\left(\frac{t}{D}\right)^2 \tag{16}$$

Equation (17) below is obtained by rewriting Equation (16) for $\epsilon_y/m$. The values of $\epsilon_y/m$ and $\epsilon_H$ that satisfy the inequality sign in Equation (17) form a region on and below a curve (b) in FIG. 16. The curve (b) in FIG. 16 is expressed by Equation (18) obtained by substituting the inequality sign in Equation (17) with an equality sign. For $\epsilon_y/m$ and $\epsilon_H$ on the curve (b), the compressive critical strain $\epsilon_{cr}$ that can be applied to the steel pipe is equal to the starting strain of strain-hardening $\epsilon_{req}$.

$$\frac{\varepsilon_y}{m} \le \left\{\varepsilon_H + \frac{16}{9\varepsilon_H}\left(\frac{t}{D}\right)^2\right\} \tag{17}$$

$$\frac{\varepsilon_y}{m} = \left\{\varepsilon_H + \frac{16}{9\varepsilon_H}\left(\frac{t}{D}\right)^2\right\} \tag{18}$$

The coordinate $(\epsilon_H)A$ on the abscissa of the intersection A between the straight line (a) and the curve (b) is the required critical strain $\epsilon_{req}$ given. The coordinate $(\epsilon_y/m)A$ on the ordinate is expressed by Equation (19) below by substituting the given required critical strain $\epsilon_{req}$ in Equation (18) above:

$$\left(\frac{\varepsilon_y}{m}\right)_A = \left\{\varepsilon_{req} + \frac{16}{9\varepsilon_{req}}\left(\frac{t}{D}\right)^2\right\} \tag{19}$$

According to Equation (17) and the curve (b) indicating this in FIG. 16, it appears as if the starting strain of strain-hardening $\epsilon_H$ is allowed to increase without limitation. However, the starting strain of strain-hardening $\epsilon_H$ defines the length of the yield plateau, and there is naturally a maximum value. This maximum value is discussed next.

Equation (20) below, which is a quadratic equation for $\epsilon_H$, is obtained by rewriting Equation (17) for the starting strain of strain-hardening $\epsilon_H$:

$$0 \le \left\{\varepsilon_H^2 - \frac{\varepsilon_y}{m}\varepsilon_H + \frac{16}{9}\left(\frac{t}{D}\right)^2\right\} \tag{20}$$

In order for the quadratic equation (20) to have a real root, the discriminant must be positive, as shown in Equation (21). The relationship between $\epsilon_y/m$ and $t/D$ then can be expressed by Equation (22). Equation (22) indicates the domain of the curve (b) for the ordinate, and the minimum value for the ordinate of the curve (b) is expressed by Equation (23). Equation (23) is the coordinate of the point B on the curve (b) on the ordinate.

$$0 \le \left\{\left(\frac{\varepsilon_y}{m}\right)^2 - 4\frac{16}{9}\left(\frac{t}{D}\right)^2\right\} \tag{21}$$

-continued $$\frac{\varepsilon_y}{m} \geq \frac{8}{3}\left(\frac{t}{D}\right) \quad (22)$$

$$\left(\frac{\varepsilon_y}{m}\right)_B = \frac{8}{3}\left(\frac{t}{D}\right) \quad (23)$$

When the relationship indicated by Equation (22) is true, the range of solutions that satisfies Equation (20) is expressed by Equations (24) and (25):

$$\varepsilon_H \leq \left\{\frac{\varepsilon_y}{2m} - \sqrt{\left(\frac{\varepsilon_y}{2m}\right)^2 - \frac{16}{9}\left(\frac{t}{D}\right)^2}\right\} \quad (24)$$

$$\left\{\frac{\varepsilon_y}{2m} + \sqrt{\left(\frac{\varepsilon_y}{2m}\right)^2 - \frac{16}{9}\left(\frac{t}{D}\right)^2}\right\} \leq \varepsilon_H \quad (25)$$

Equation (24) shows that $\varepsilon_H$ is a finite value while Equation (25) allows $\varepsilon_H$ to be infinite. Since $\varepsilon_H$ is a finite value, Equation (24) is employed as a solution of Equation (20) while Equation (25) is dismissed. Substitution of the minimum value of $\varepsilon_y/m$ given by Equation (23) allows the coordinate on the abscissa of the point B on the curve (b) to be determined by Equation (26):

$$(\varepsilon_H)_B = \frac{4}{3}\left(\frac{t}{D}\right) \quad (26)$$

The coordinate $(\varepsilon_H)B$ of the point B on the curve (b) on the abscissa expressed by Equation (26) indicates the maximum compressive critical strain $\varepsilon_{crmax}$. Thus, when the straight line (a) is shifted downward in parallel, the limit value of shifting the line downward in parallel is when the straight line shifted in parallel passes through the point B. Thus, this straight line is referred to as "straight line (c)" below and the equation that indicates the straight line (c) is pursued in the description below.

Assume that the straight line (c) is expressed as Equation (27) below:

$$\frac{\varepsilon_y}{m} = \varepsilon_H + c \quad (27)$$

wherein c is a value of a segment on the ordinate.

Since the straight line (c) passes through the point B, the coordinate of the point B is substituted in Equation (27) so that Equation (27) is expressed by Equation (28):

$$\frac{\varepsilon_y}{m} = \varepsilon_H + \frac{4}{3}\left(\frac{t}{D}\right) \quad (28)$$

(C) That the starting strain of strain-hardening is larger than the yield strain The condition that the starting strain of strain-hardening is larger than the yield strain is given by Equation (29) below:

$$\varepsilon_y \leq \varepsilon_H \quad (29)$$

A straight line (d) in FIG. 16 indicates $\varepsilon_H = \varepsilon_y$. Since the necessary condition is that the starting strain of strain-hardening $\varepsilon_H$ is larger than the yield strain $\varepsilon_y$, the region of solutions lies at the right-hand side of the straight line (d).

The solution region is determined as above as shown in FIG. 16. In order to evaluate whether a steel pipe whose pipe diameter D and pipe thickness t are known gives a compressive critical strain $\varepsilon_{cr}$ larger than the required critical strain $\varepsilon_{req}$, it is sufficient if whether the yield strain $\varepsilon_y$, the modulus of strain-hardening m, and the starting strain of strain-hardening $\varepsilon_H$ of the stress-strain curve lie in a region defined by the straight lines (a), (c), and (d), and the curve (b) is determined.

The following two equations show this relationship. These equations are equations of (16) of the present invention:

$$\left\{\varepsilon_H + \frac{4}{3}\left(\frac{t}{D}\right)\right\} \leq \frac{\varepsilon_y}{m} \leq \left\{\varepsilon_H + \frac{16}{9\varepsilon_{req}}\left(\frac{t}{D}\right)^2\right\} \quad (30)$$

wherein $$\varepsilon_y \leq \varepsilon_H \leq \varepsilon_{req}$$

and $$\left\{\varepsilon_H + \frac{4}{3}\left(\frac{t}{D}\right)\right\} \leq \frac{\varepsilon_y}{m} \leq \left\{\varepsilon_H + \frac{16}{9\varepsilon_H}\left(\frac{t}{D}\right)^2\right\} \quad (31)$$

wherein $$\varepsilon_{req} < \varepsilon_H < \frac{4}{3}\left(\frac{t}{D}\right).$$

(17) A method for designing a material of a steel pipe of the present invention is a method for designing a material for a steel pipe, pipe diameter D, pipe thickness t, and required critical strain $\varepsilon_{req}$ of which are given, characterized in that, in determining a stress-strain relationship of a material having a yield plateau in the stress-strain relationship, the yield strain $\varepsilon_y$, the modulus of strain-hardening m, and the starting strain of strain-hardening $\varepsilon_H$ of a stress-strain curve of the obtained stress-strain relationship are determined such that the yield strain $\varepsilon_y$, the modulus of strain-hardening m, and the starting strain of strain-hardening $\varepsilon_H$ of a material to be designed are in a range defined by equations below in a coordinate plane with an ordinate indicating $\varepsilon_y/m$ and an abscissa indicating $\varepsilon_H$:

$$\left\{\varepsilon_H + \frac{4}{3}\left(\frac{t}{D}\right)\right\} \leq \frac{\varepsilon_y}{m} \leq \left\{\varepsilon_H + \frac{16}{9\varepsilon_{req}}\left(\frac{t}{D}\right)^2\right\} \quad (30)$$

wherein $$\varepsilon_y \leq \varepsilon_H \leq \varepsilon_{req}$$

and $$\left\{\varepsilon_H + \frac{4}{3}\left(\frac{t}{D}\right)\right\} \leq \frac{\varepsilon_y}{m} \leq \left\{\varepsilon_H + \frac{16}{9\varepsilon_H}\left(\frac{t}{D}\right)^2\right\} \quad (31)$$

wherein $$\varepsilon_{req} < \varepsilon_H < \frac{4}{3}\left(\frac{t}{D}\right).$$

(18) A steel pipe of the present invention is characterized in being designed by the method for designing the material of the steel pipe according to (17) above.

(19) A steel pipe of the present invention is a steel pipe evaluated as being applicable to a structure that requires plastic design by the method for evaluating local buckling performance of the steel pipe according to any one of (1) to (12), (16) and (17) above.

BEST MODE FOR CARRYING OUT THE INVENTION

First Embodiment

In this embodiment, an example of evaluating whether a steel pipe having a pipe diameter/pipe thickness ratio (D/t) of 50 is applicable to a pipeline with required critical strain $\epsilon_{req}$=1.5% is described.

Figure 1:
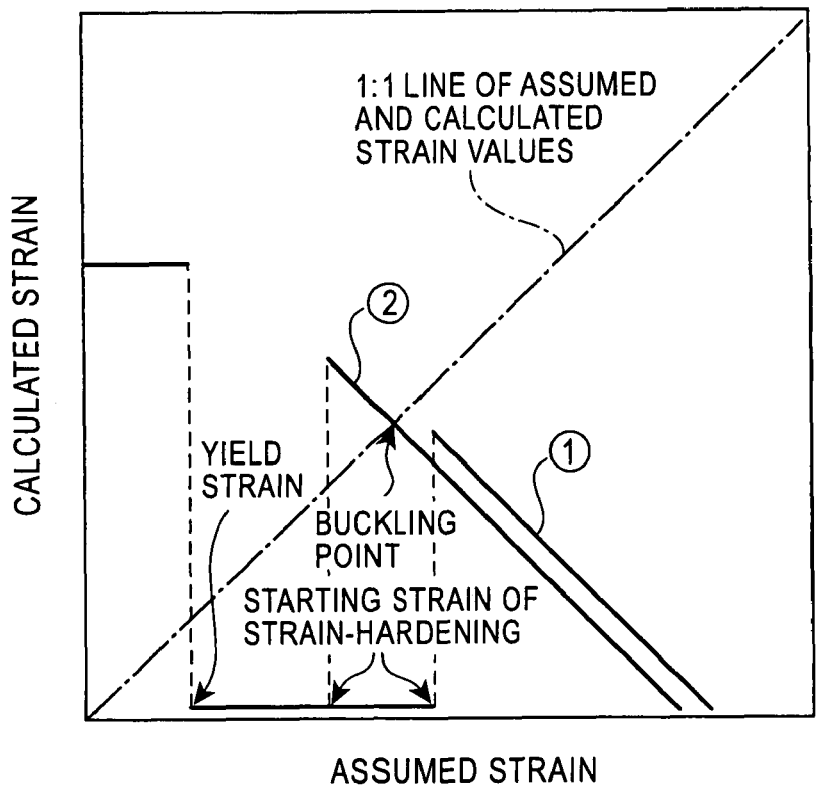
FIG. 1 is a diagram for explaining a method for evaluating local buckling performance of a steel pipe according to the present invention (No. 1).
Figure 2:
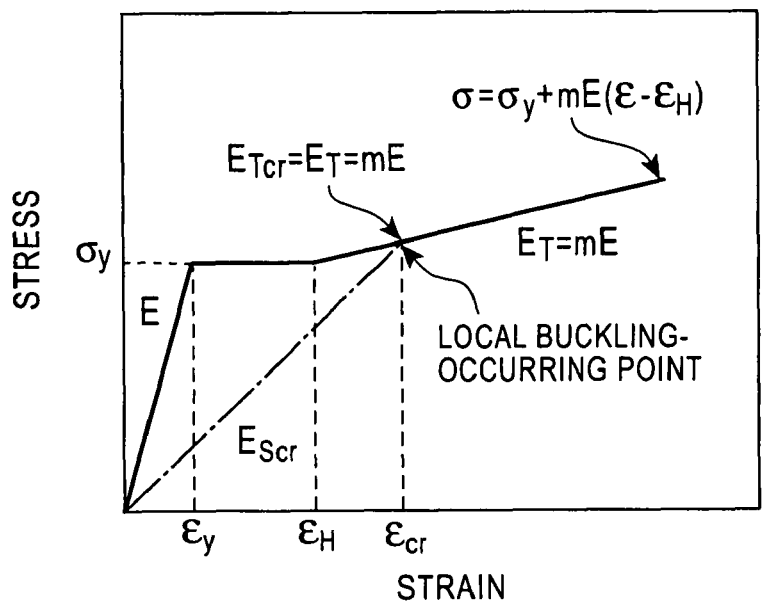
FIG. 2 is a diagram for explaining a method for evaluating local buckling performance of a steel pipe according to the present invention (No. 2).
Figure 3:
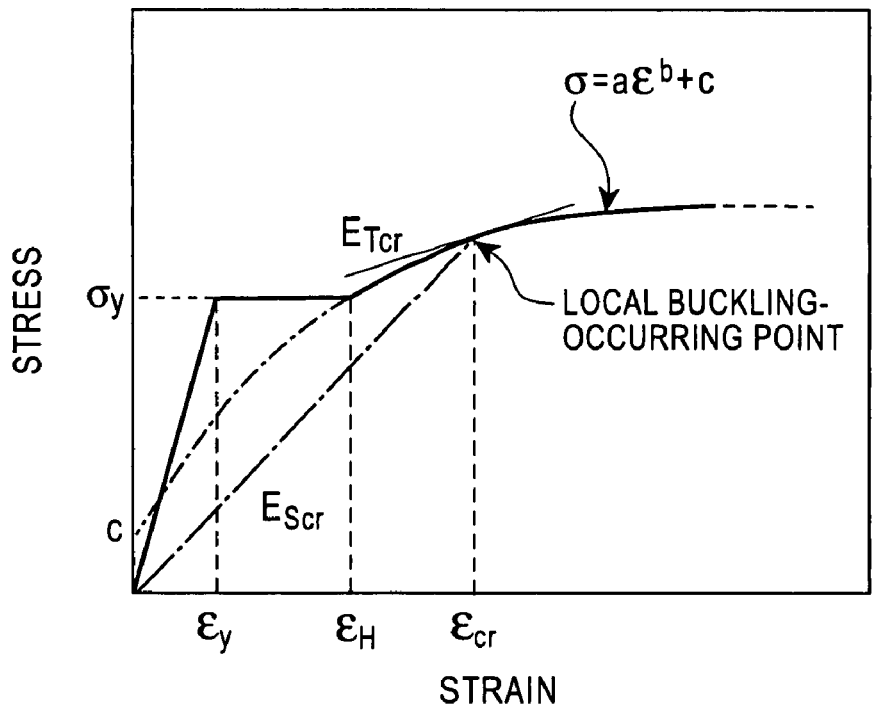
FIG. 3 is a diagram for explaining a method for evaluating local buckling performance of a steel pipe according to the present invention (No. 3).
Figure 4:
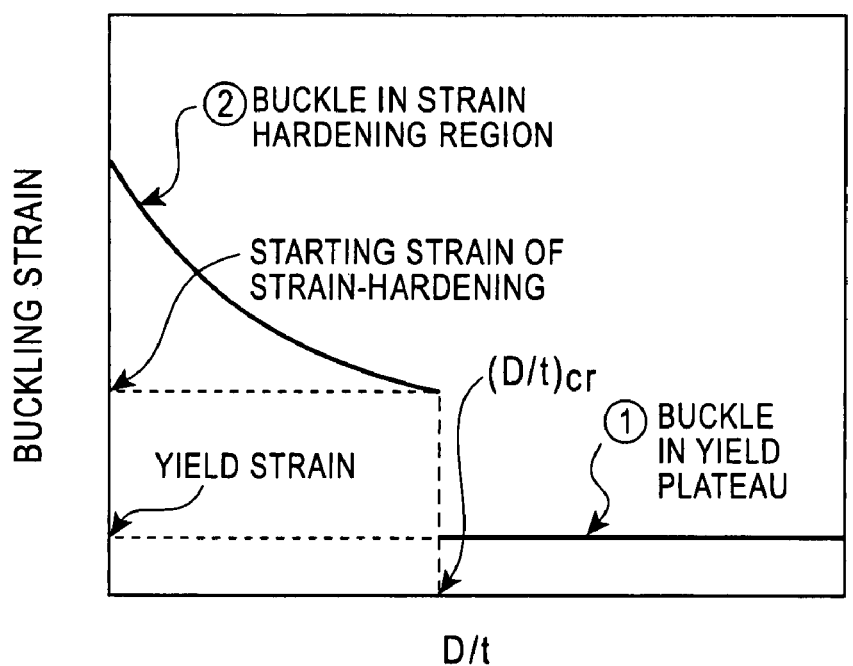
FIG. 4 is a diagram for explaining a method for evaluating local buckling performance of a steel pipe according to the present invention (No. 4).
Figure 5:
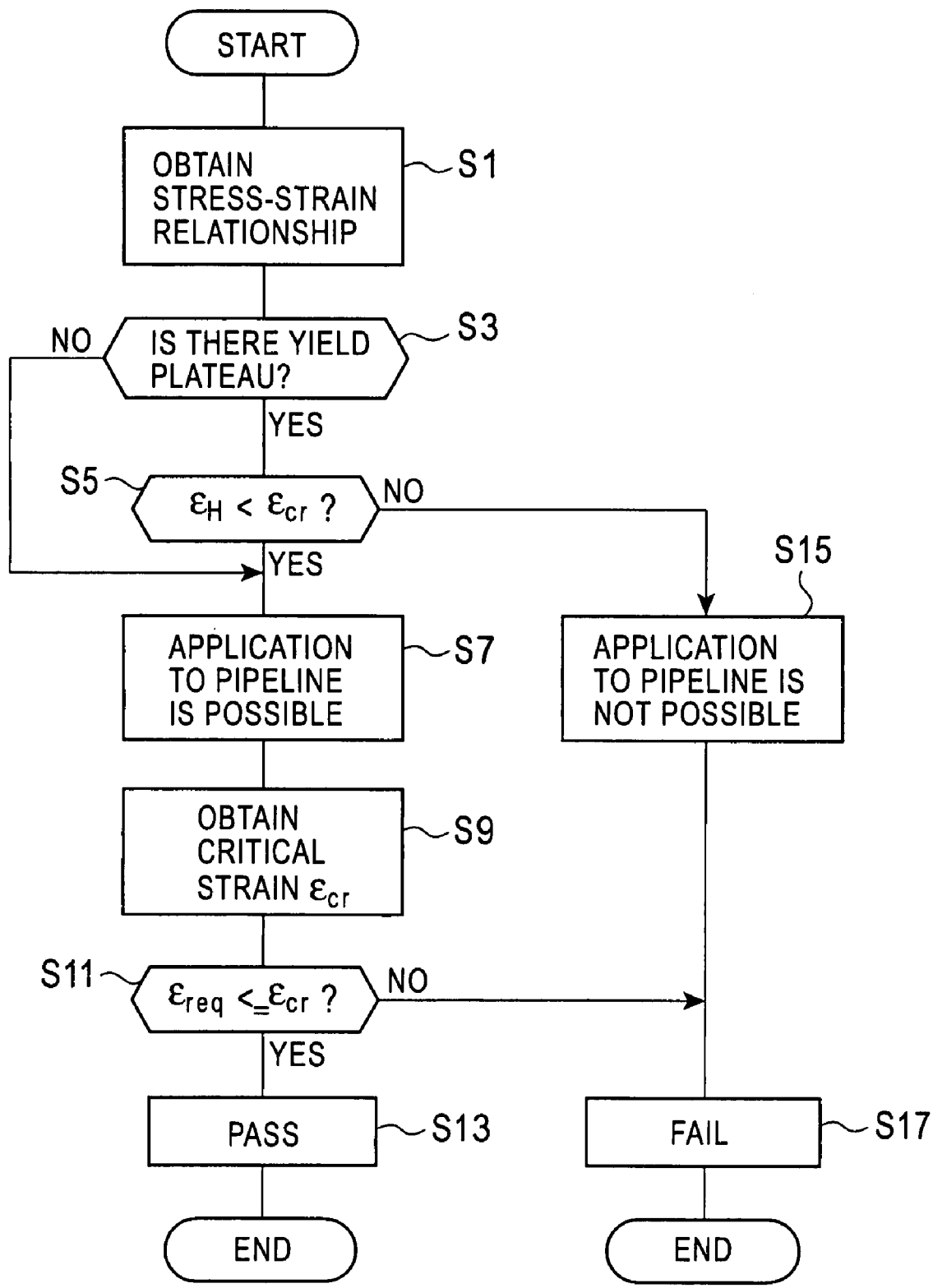
FIG. 5 is a flowchart of a first embodiment of the present invention.

FIG. 5 is a flowchart showing the flow of an evaluation method of this embodiment. The embodiment is described below with reference to FIG. 5.

First, a stress-strain relationship of a steel pipe material to be evaluated is obtained (S1). As the method for obtaining the stress-strain relationship, a tensile test using a sample specimen may be conducted or, when experimental data already exists, the experimental data may be downloaded from a database storing the data.

Based on the obtained stress-strain relationship, whether the steel pipe is a yield plateau model having a yield plateau on the stress-strain curve or a continuous hardening model is determined (S3). If the steel pipe is determined to be a continuous hardening model in the determination in S3, then the pipe is determined to have a possibility of application to pipelines since the continuous hardening model has excellent buckling performance (S7).

On the other hand, when the pipe is determined to be a yield plateau model in the determination in S3, the starting strain of strain-hardening $\epsilon_H$ of this steel pipe material is obtained from the stress-strain relationship of the steel material obtained in S1, and the comparison of the starting strain of strain-hardening $\epsilon_H$ and the critical strain $\epsilon_{cr}$ of the steel pipe composed of the material is determined (S5).

In this embodiment, the pipe is determined to be a yield plateau model in determination of (S3). Thus, determination of (S5) is conducted. Furthermore, in this embodiment, the shape of the strain-hardening region in the stress-strain relationship (stress-strain curve) obtained in (S1) is applicable to the linear hardening rule; thus, the determination in (5) is conducted on the basis of Equation (2.1) below described above:

$$\varepsilon_{cr} = \frac{16}{9(\varepsilon_y/m - \varepsilon_H)}\left(\frac{t}{D}\right)^2 \quad (2.1)$$

That is, the computed value at the right-hand side of Equation (2.1) is compared with the starting strain of strain-hardening $\epsilon_H$, and if the computed value is larger than the starting strain of strain-hardening $\epsilon_H$, then the critical strain $\epsilon_{cr}$ is determined to be larger than the starting strain of strain-hardening $\epsilon_H$.

Specific figures to be substituted in the right-hand side of Equation (2.1) will now be discussed. (t/D) is already given, i.e., (t/D)=1/50. The starting strain of strain-hardening $\epsilon_H$ can be found from the stress-strain relationship obtained in (S1) and is 1.5% in this example. The yield strain $\epsilon_y$ can also be found from the stress-strain relationship obtained in S1 and is 0.22% in this example. The modulus of strain-hardening m can also be determined from the stress-strain relationship obtained in S1 and m=0.04.

These values are substituted in the right-hand side of Equation (2.1), and the computed value is 1.78%. This computed value, 1.78%, is compared with the starting strain of strain-hardening $\epsilon_n$=1.5%. The computed value is larger. Thus, the critical strain EC: is determined to be larger than the starting strain of strain-hardening $\epsilon_{cr}$ (S5), and possibility of application to pipelines is affirmed (S7).

Once the possibility of application to pipelines is affirmed, the critical strain $\epsilon_{cr}$ of the steel pipe is obtained (S9). In this example, since the computed value in (S5) is the critical strain $\epsilon_{cr}$ of the steel pipe, further computation or the like is not necessary. The obtained critical strain $\epsilon_{cr}$ is compared with the required critical strain $\epsilon_{req}$ (S1). If the critical strain $\epsilon_{cr}$ is larger than the required critical strain $\epsilon_{req}$, then it is determined as PASS (S13). Since critical strain $\epsilon_{cr}$=1.78% and required critical strain $\epsilon_{req}$=1.5%, the critical strain $\epsilon_{cr}$ is larger than the required critical strain $\epsilon_{req}$ in this example, and the steel pipe is determined as PASS.

When the critical strain $\epsilon_{cr}$ is determined to be not larger than the starting strain of strain-hardening $\epsilon_H$ in (S5), the steel pipe is determined as inapplicable to pipelines (S15) and is determined as FAIL (S17). When the critical strain $\epsilon_{cr}$ is not larger than the required critical strain $\epsilon_{req}$ in (S11), the steel pipe is also determined as FAIL (S17).

As is described above, according to this embodiment, whether the steel pipe to be evaluated has high local buckling performance can be easily evaluated. Thus, for example, in producing a continuous hardening model-steel pipe as pipelines, even when the steel pipe undergoes material change by heat treatment in a coating step during the production and transforms into a yield plateau model, whether the steel pipe can be treated equally with the continuous hardening model can be easily evaluated by evaluating the buckling performance of the steel pipe.

Note that although the comparison of the critical strain $\epsilon_{cr}$ and the starting strain of strain-hardening $\epsilon_H$ is determined on the basis of Equation (2.1) in (S5) in the example above, the present invention is not limited to this. Alternatively, for example, an experimental steel pipe identical to the steel pipe to be evaluated may be put under a load that generates a strain corresponding to the starting strain of strain-hardening to determine whether the experimental steel pipe undergoes local buckling. If the experimental steel pipe undergoes local buckling, then the starting strain of strain-hardening may be determined to be not less than critical strain $\epsilon_{cr}$' and if no local buckling occurs, then the critical strain $\epsilon_{cr}$ may be determined to be larger than the starting strain of strain-hardening.

Alternatively, the determination may be made on the basis of Equation (1.1) described above.

In the cases where the stress-strain curve in the strain-hardening region in the stress-strain relationship of the steel pipe to be evaluated obtained in (S1) can be approximated by a power-law function, determination is made on the basis of Equation (3.1).

As yet another modification of step S5, the critical strain may be calculated using Equation (1.1), Equation (2.1), Equation (3.1), or the like and the calculated critical strain $\epsilon_{cr}$ may be directly compared with the starting strain of strain-hardening $\epsilon_H$. In such a case, step S9 is omitted. Moreover, according to Equation (1.1), the value of critical strain cannot be calculated if the critical strain lies in the yield plateau region; thus determination of step S5 may be made by utilizing this phenomenon. That is, the stress-strain relationship is input to Equation (1.1), and if the critical strain is incomputable, then NO is selected in step S5. If the critical strain is computed, then YES is selected in step S5.

Second Embodiment

In this embodiment, an evaluation method different from that of the first embodiment is described using an example of determining whether a steel pipe to be evaluated identical to the first embodiment is applicable to a pipeline with required critical strain $\epsilon_{req}$=1.5%.

Figure 6:
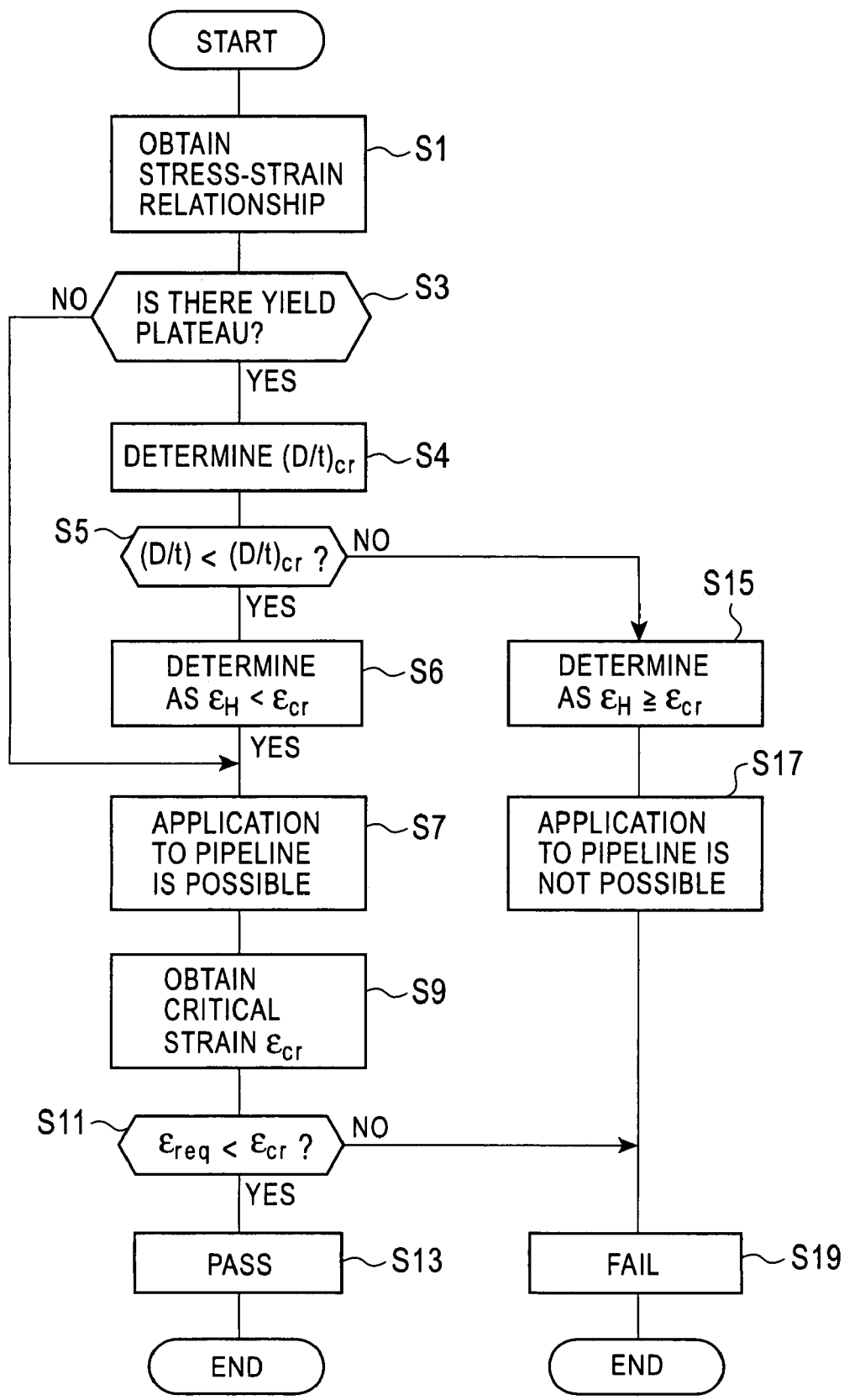
FIG. 6 is a flowchart of a second embodiment of the present invention.

FIG. 6 shows a flowchart showing the flow of the evaluation method of this embodiment. The embodiment is described below with reference to FIG. 6.

The stress-strain relationship of a steel material is obtained (S1), and whether the steel material is a yield plateau model or a continuous hardening model is determined (S3). These steps are the same as those in the first embodiment.

When the material is determined to be the yield plateau model in (S3), then the pipe diameter/pipe thickness ratio $(D/t)_{cr}$ at which the critical strain of the steel pipe becomes the same as the starting strain of strain-hardening in the stress-strain relationship of the steel pipe obtained in (S1) is determined (S4). The comparison of the determined pipe diameter/pipe thickness ratio $(D/t)_{cr}$ and the pipe diameter/pipe thickness ratio $(D/t)$ is then determined (S5).

In this embodiment, since the shape of the strain-hardening region in the stress-strain relationship obtained in (S1) is applicable to the linear hardening rule, determination in (S5) is conducted on the basis of Equation (4.1) below described above:

$$\left(\frac{D}{t}\right)_{cr} = \frac{4}{3\sqrt{(\varepsilon_y/m - \varepsilon_H)\varepsilon_H}} \quad (4.1)$$

When $\epsilon_H$=1.5%, $\epsilon_y$=0.22%, and m=0.04 are substituted in the right-hand side of Equation (4.1) to conduct computation, $(D/t)_{cr}$=54.4. Since D/t=50, $(D/t)<(D/t)_{cr}$ holds true. Thus, the critical strain $\epsilon_{cr}$ is determined to be larger than the starting strain of strain-hardening $\epsilon_H$ (S6), and applicability to pipeline is affirmed (S7). Steps S9 and S11 are conducted as in the first embodiment, and, finally, evaluation of PASS is rendered as in the first embodiment (S13).

In determination of (S5), when $(D/t) \geq (D/t)_{cr}$, the critical strain $\epsilon_{cr}$ is determined to be not larger than the starting strain of strain-hardening $\epsilon_H$ (S15), applicability to pipelines is denied (S17), and, finally, evaluation of FAIL is rendered (S19).

As described above, as in the first embodiment, whether the steel pipe to be evaluated has high local buckling performance can be easily evaluated according to this embodiment. Furthermore, since the pipe diameter/pipe thickness ratio (D/t), which is an easily comprehensible parameter, is used as the standard for evaluating local buckling performance, evaluation is easy.

Note that although the comparison of the pipe diameter/pipe thickness ratio $(D/t)_{cr}$ and the pipe diameter/pipe thickness ratio (D/t) of the steel pipe to be evaluated in (S5) is determined on the basis of Equation (4.1), the present invention is not limited to this. In the cases where the stress-strain curve in the strain-hardening region in the stress-strain relationship of the steel pipe to be evaluated obtained in (S1) can be approximated by a power-law function, determination is made on the basis of Equation (5.1) described above.

Although the local buckling performance of a particular steel pipe that already exists is evaluated in this embodiment, as long as a steel material to be used is determined, the pipe diameter/pipe thickness ratio $(D/t)_{cr}$ that corresponds to the starting strain of strain-hardening in the stress-strain relationship of the steel material can be determined so that this can be used as the design guideline of how large the pipe diameter/pipe thickness ratio (D/t) can be, i.e., how thin the pipe can be, in designing the steel pipe for pipelines. A method for designing a steel pipe based on this idea is described in a third embodiment below.

Third Embodiment

Figure 7:
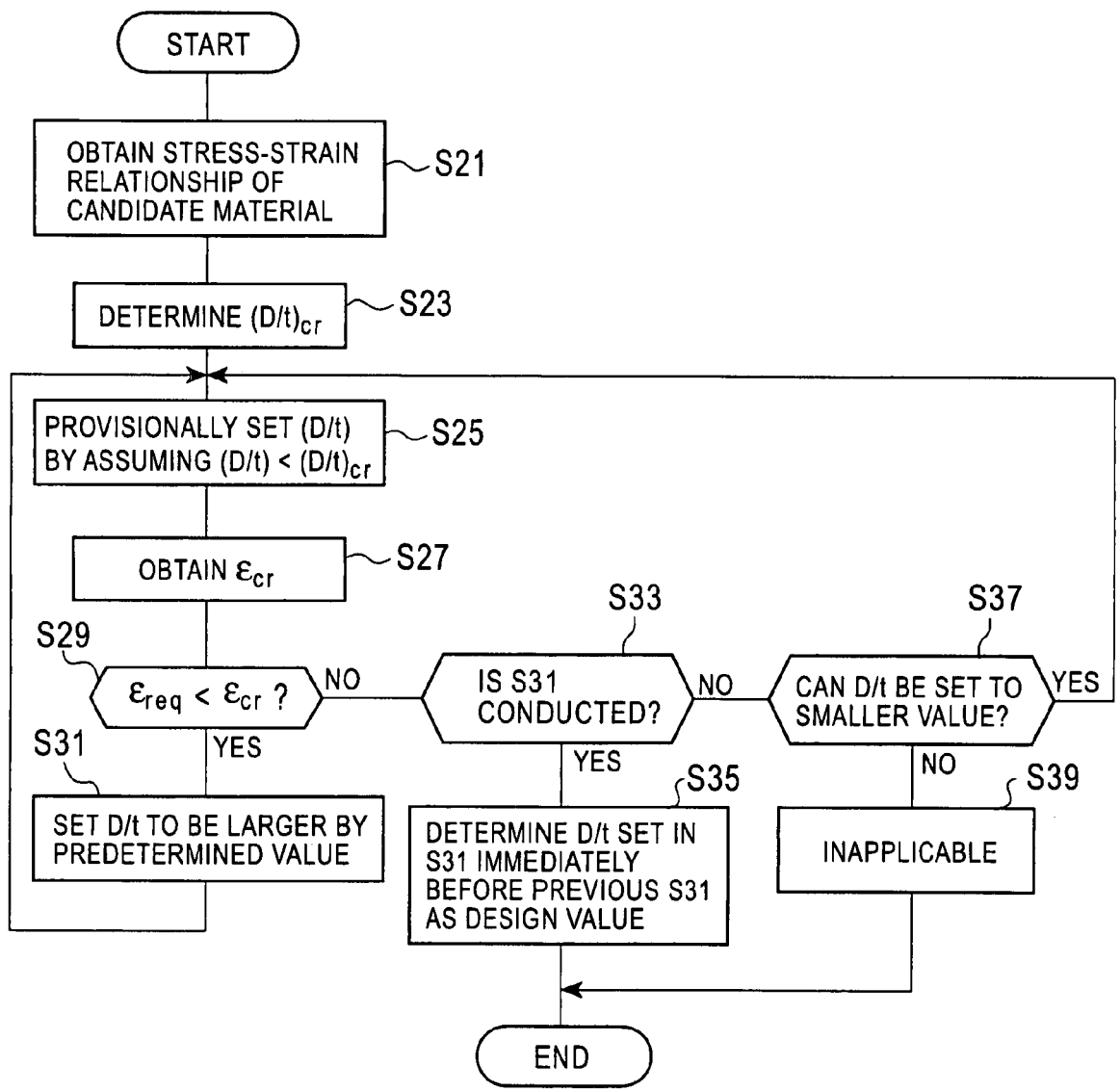
FIG. 7 is a flowchart of a third embodiment of the present invention.

FIG. 7 is a flowchart showing the flow of a method for designing a steel pipe according to this embodiment. This embodiment is described with reference to FIG. 7.

The stress-strain relationship of a candidate material having a yield plateau is obtained (S21). The step S21 is the same as step S1 in the first embodiment.

Using the stress-strain relationship obtained in S21, $(D/t)_{cr}$ is determined (S23). An example of the method for determining $(D/t)_{cr}$ is a method using Equation (1.1) below described above:

$$\varepsilon_{cr} = \frac{4}{3}\sqrt{\frac{E_{Tcr}}{E_{Scr}}}\frac{t}{D} \quad (1.1)$$

Equation (1.1) means that the value in the left-hand side is the critical strain when the equality is true. Thus, in order for the steel pipe to undergo local buckling at a starting strain of strain-hardening in the stress-strain relationship determined in S21, the starting strain of strain-hardening should be substituted in the left-hand side of Equation (1.1), the secant modulus $(E_S)$ and the tangent modulus $(E_T)$ should be calculated at a point on the stress-strain relationship corresponding to the starting strain of strain-hardening, and these values should be substituted in the right-hand side of Equation (1.1) to determine the pipe diameter/pipe thickness ratio (D/t) at which the equality is true.

Another method is to use Equation (4.1) below for determination when the strain-hardening region in the stress-strain relationship obtained in S21 can be linearly approximated and to use Equation (5.1) below for determination when the strain-hardening region in the stress-strain relationship obtained in S21 can be approximated by a power-law function:

$$\left(\frac{D}{t}\right)_{cr} = \frac{4}{3\sqrt{(\varepsilon_y/m - \varepsilon_H)\varepsilon_H}} \quad (4.1)$$

wherein $(D/t)_{cr}$: maximum pipe diameter/pipe thickness ratio
$\epsilon_y$: yield strain
$\epsilon_H$: starting strain of strain-hardening
m: modulus of strain-hardening $$\left(\frac{D}{t}\right)_{cr} = \frac{4}{3\varepsilon_H}\sqrt{\left(1 - \frac{c}{\sigma_y}\right)b} \quad (5.1)$$

wherein $(D/t)_{cr}$: maximum pipe diameter/pipe thickness ratio
$\epsilon_y$: yield strain
$\epsilon_H$: starting strain of strain-hardening
m: modulus of strain-hardening.

Next, D/t of the steel pipe to be designed is provisionally set (S25). Here, the condition that D/t should satisfy is D/t<$(D/t)_{cr}$.

Note that in designing a steel pipe for pipelines, it is necessary to provisionally set pipe diameter D and pipe thickness t that minimizes the operation cost and construction cost on the basis of the amount of compressed fluid to be transported via pipelines and the distance of the transportation. Thus, D/t<$(D/t)_{cr}$ is a necessary condition among design conditions.

On the basis of D/t provisionally set, the critical strain $\epsilon_{cr}$ of the steel pipe designed using the material is obtained (S27).

Any one of the methods described in (2) in which Equation (1.1) is used, (4) in which Equation (2.1) is used, and (5) in which Equation (3.1) is used can be used as the method for determining the critical strain $\epsilon_{cr}$.

Whether $\epsilon_{req} < \epsilon_{cr}$ is satisfied is determined by comparing $\epsilon_{cr}$ obtained in S27 with the required critical strain $\epsilon_{req}$, which is the critical strain required (S29).

Note that the required critical strain $\epsilon_{req}$ is set by designing the structure of a pipeline while taking into account the construction layout of the pipe having diameter and thickness provisionally set in S25, determining the maximum strain that occurs in the pipe when the transportation pressure, ground movements, or external force is applied to the designed pipeline structure, and considering a particular margin of safety for the maximum strain.

When YES is selected in evaluation in S29, i.e., when $\epsilon_{req} < \epsilon_{cr}$ is satisfied, the setting of D/t is increased by one rank to further reduce the thickness of the steel pipe (S31). Here, the ratio of increasing D/t is a predetermined value based on appropriate conditions, such as the magnitude of the difference between $\epsilon_{req}$ and $\epsilon_{cr}$ obtained in S27 or a particular value set in advance.

If D/t is reset in S31, then the steps from S27 and on are repeated while confirming D/t<$(D/t)_{cr}$ is satisfied in S25.

When NO is selected in evaluation in S29, i.e., when $\epsilon_{req} < \epsilon_{cr}$ is not satisfied, whether the process has gone through S31 is determined (S33). If YES is selected, i.e., if S31 is performed, D/t set in S31 immediately before the previous S31 is determined as the design value (S35).

Once the design value of D/t is determined, a steel pipe that satisfies a predetermined required critical strain can be produced by conducting steel pipe production based on the design value.

When No is selected in determination in S33, i.e., when S31 is not performed, the process returns to S25 to determine whether D/t can be set to a further smaller value (S37). That is, since D/t is assumed to satisfy D/t<$(D/t)_{cr}$ and the diameter D and the thickness t of the pipe are provisionally set to minimize the operation cost and construction cost on the basis of the amount of compressed fluid to be transported via the pipeline and the distance of transportation in the provisional setting in S25, whether D/t can be set to a value smaller than the value set in the previous step is determined while relaxing the operation and construction cost conditions, for example.

If YES is selected in S37, i.e., if resetting of D/t is possible, then the process returns to S25 to repeat the same steps. If NO is selected in S37, i.e., if resetting of D/t is not possible, the application of the material to the concerned usage is denied (S39).

As described above, in this embodiment, even a material having a yield plateau can be treated as if it is a continuous hardening-type material in designing the optimum pipe diameter/pipe thickness ratio (D/t) since the process shown in FIG. 7 is appropriately conducted while considering the pipe diameter/pipe thickness ratio $(D/t)_{cr}$, i.e., while adjusting the value of pipe diameter/pipe thickness ratio (D/t) in a manner that (D/t)<$D/t)_{cr}$ is always satisfied.

Fourth Embodiment

In this embodiment, nine types of materials having stress-strain relationships shown in Table 1 were used to produce steel pipes having an outer diameter D=762.0 mm and a pipe thickness t=15.24 mm (D/t=50). Evaluation of whether the steel pipe can be used as a steel pipe for X80-grade linepipes with required critical strain area $\epsilon_{req}$=0.5% was conducted based on the present invention. Whether the evaluation was appropriate was inspected by FEM analysis.

TABLE 1

| Case | $\epsilon_y$ | m | $\epsilon_H$ | (D/t)max |
|---|---|---|---|---|
| P-1 | 0.0029 | 0.015 | 0.003 | 55.7 |
| P-2 | 0.0029 | 0.020 | 0.003 | 64.5 |
| P-3 | 0.0029 | 0.025 | 0.003 | 72.3 |
| P-4 | 0.0029 | 0.015 | 0.005 | 43.4 |
| P-5 | 0.0029 | 0.020 | 0.005 | 50.3 |
| P-6 | 0.0029 | 0.025 | 0.005 | 56.5 |
| P-7 | 0.0029 | 0.015 | 0.010 | 31.1 |
| P-8 | 0.0029 | 0.020 | 0.010 | 36.2 |
| P-9 | 0.0029 | 0.025 | 0.010 | 40.9 |

Figure 17:
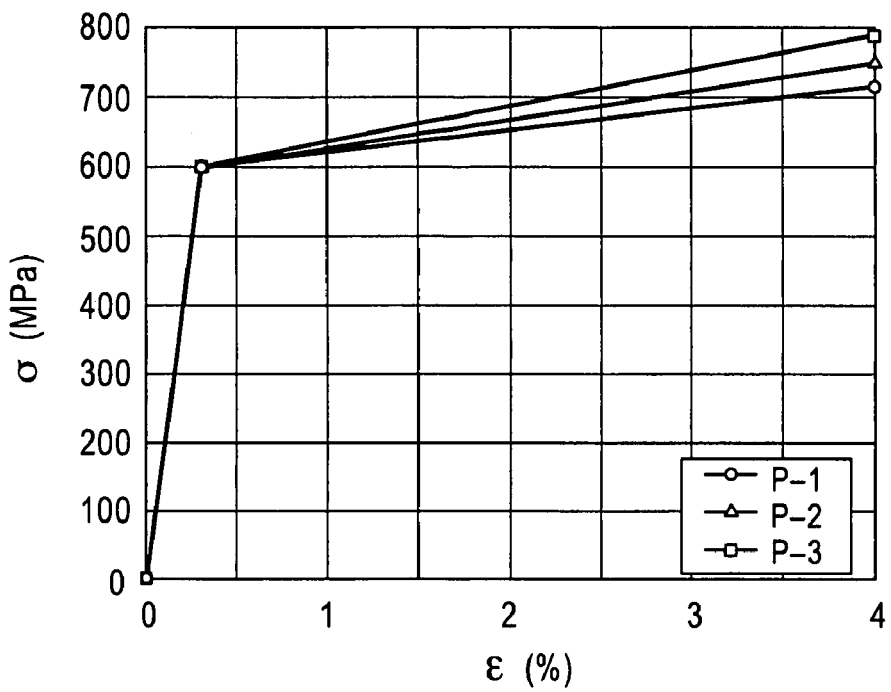
FIG. 17 shows stress-strain curves of materials evaluated in the fourth embodiment of the present invention (No. 1).
Figure 18:
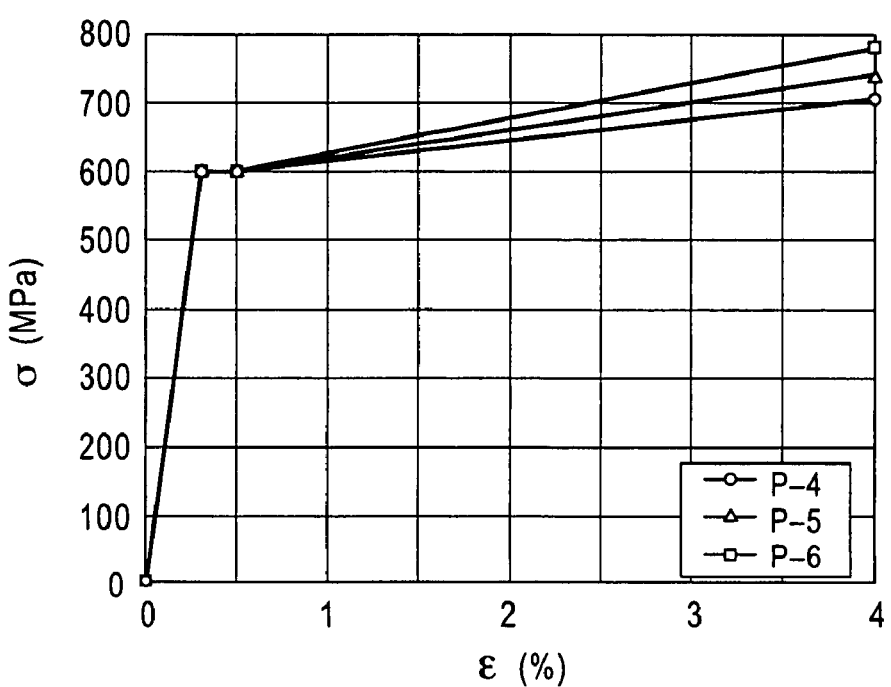
FIG. 18 shows stress-strain curves of materials evaluated in the fourth embodiment of the present invention (No. 2).
Figure 19:
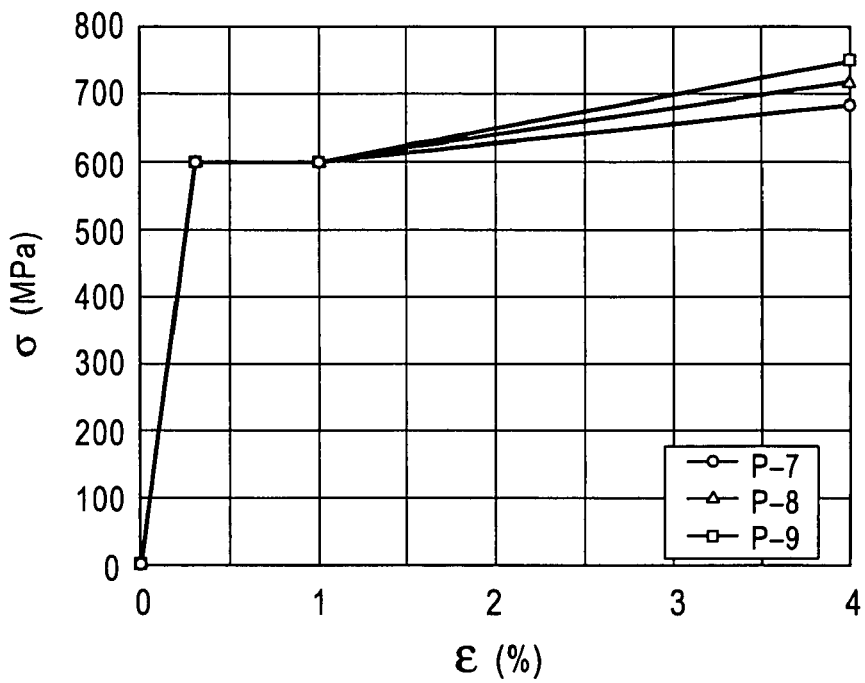
FIG. 19 shows stress-strain curves of materials evaluated in the fourth embodiment of the present invention (No. 3).

Table 1 shows stress-strain relationships of nine types of materials related to X80-grade linepipes. The yield strain $\epsilon_y$ of each material is 0.0029 (0.29%), and the starting strain of strain-hardening $\epsilon_H$ is 0.003 (0.3%), 0.005 (0.5%), or 0.010 (1.0%). The modulus m of modulus of strain-hardening mE is set to 0.015, 0.020, or 0.025. (D/t)$_{max}$ shown in Table 1 is the value obtained by substituting these values in Equation (12). The stress-strain curves corresponding to P-1 to P-9 are shown in FIGS. 17, 18, and 19.

Figure 20:
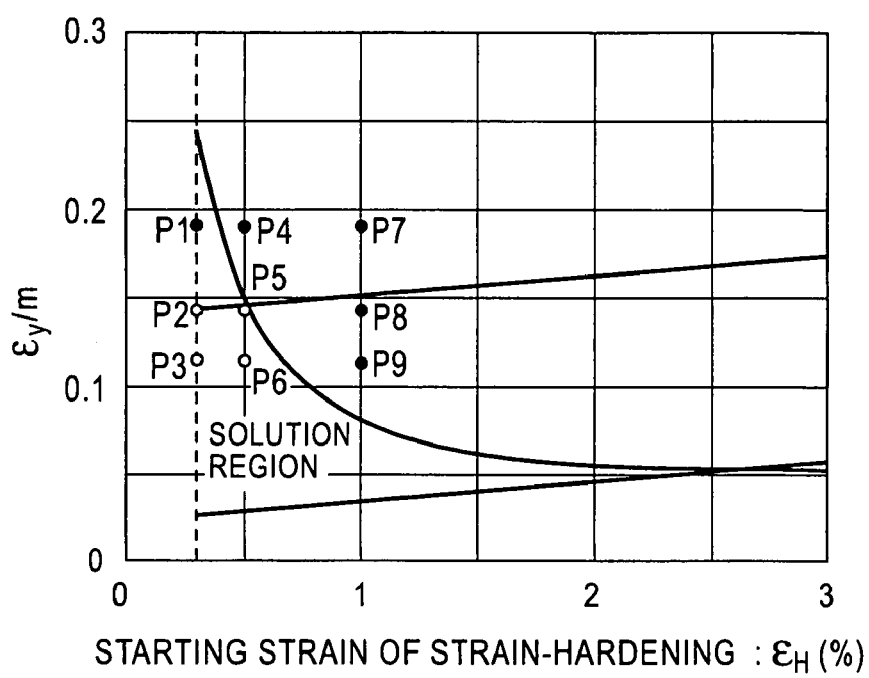
FIG. 20 is a graph showing a region related to a method for evaluating local buckling performance according to the fourth embodiment of the present invention.

FIG. 20 shows a region defined by the following equation in a coordinate plane with the ordinate indicating $\epsilon_y/m$ and the abscissa indicating $\epsilon_H$ while substituting D=762.0 mm, t=15.24 mm, $\epsilon_y$=0.29%, and $\epsilon_{req}$=0.5% in the following equation indicating the method for evaluating local buckling performance of a yield plateau model:

$$\left\{\varepsilon_H + \frac{4}{3}\left(\frac{t}{D}\right)\right\} \le \frac{\varepsilon_y}{m} \le \left\{\varepsilon_h + \frac{16}{9\varepsilon_{req}}\left(\frac{t}{D}\right)^2\right\} \quad (30)$$

wherein $$\varepsilon_y \le \varepsilon_H \le \varepsilon_{req}$$

and $$\left\{\varepsilon_H + \frac{4}{3}\left(\frac{t}{D}\right)\right\} \le \frac{\varepsilon_y}{m} \le \left\{\varepsilon_H + \frac{16}{9\varepsilon_H}\left(\frac{t}{D}\right)^2\right\} \quad (31)$$

wherein $$\varepsilon_{req} < \varepsilon_H < \frac{4}{3}\left(\frac{t}{D}\right).$$

In FIG. 20, coordinate points ($\epsilon_y/m$, $\epsilon_H$) of nine types of materials shown in Table 1 are respectively plotted. In FIG. 20, those in the region defined by the equations above are indicated by open circles, and those outside the region are indicated by solid circles.

As apparent from FIG. 20, P-2, P-3, P-5, and P-6 are plotted in the solution region. Thus, P-2, P-3, P-5, and P-6 are evaluated as PASS. If a steel pipe can be made under the material design conditions of these four cases, the compressive critical strain $\epsilon_{cr}$ of the steel pipe satisfies the required critical strain $\epsilon_{req}$.

Next, whether the evaluation above was correct was inspected by FEM analysis.

Buckling analysis by FEM for the steel pipe subjected to compression was set as follows: outside diameter D=762.0 mm and pipe thickness t=15.24 (D/t=50). The results of compressive buckling analysis are shown in Table 2.

TABLE 2

| Case | $\epsilon_y$ | m | $\epsilon_H$ | (D/t)max | $\epsilon$ cr (%) | Evaluation |
|---|---|---|---|---|---|---|
| P-1 | 0.0029 | 0.015 | 0.003 | 55.7 | 0.38 | FAIL |
| P-2 | 0.0029 | 0.020 | 0.003 | 64.5 | 0.58 | PASS |
| P-3 | 0.0029 | 0.025 | 0.003 | 72.3 | 0.82 | PASS |
| P-4 | 0.0029 | 0.015 | 0.005 | 43.4 | 0.30 | FAIL |
| P-5 | 0.0029 | 0.020 | 0.005 | 50.3 | 0.51 | PASS |
| P-6 | 0.0029 | 0.025 | 0.005 | 56.5 | 0.85 | PASS |
| P-7 | 0.0029 | 0.015 | 0.010 | 31.1 | 0.30 | FAIL |
| P-8 | 0.0029 | 0.020 | 0.010 | 36.2 | 0.30 | FAIL |
| P-9 | 0.0029 | 0.025 | 0.010 | 40.9 | 0.30 | FAIL |

Table 2 also shows the results of evaluation based on the region shown in FIG. 20.

As shown in Table 2, the values of the compressive critical strain $\epsilon_{cr}$ of the analytic models of these four cases, i.e., P-2, P-3, P-5, and P-6, were 0.58%, 0.82%, 0.511%, and 0.85%, respectively.

Thus, in the four cases, P-2, P-3, P-5, and P-6, the critical strain is larger than the required critical strain (0.5%).

As apparent from Table 2, the results are consistent with the results that evaluated the four cases, P-2, P-3, P-5, and P-6, as PASS using the region shown in FIG. 20.

Therefore, evaluation by the present invention is consistent with the results of the FEM analysis, which Droves the effectiveness of the present invention.

Fifth Embodiment

In this embodiment, ten types of materials having stress-strain relationships shown in Table 3 were used to produce steel pipes having an outside diameter D=762.0 mm and a pipe thickness t=15.6 mm (D/t=48.8). Evaluation of whether the steel pipe can be used as a steel pipe for X80-grade linepipes with required critical strain $\epsilon_{req}$=0.5% was conducted based on the present invention.

Furthermore, the materials shown in Table 3 were used to produce steel pipes having an outside diameter D=914.4 mm and a pipe thickness t=15.2 mm. Evaluation of whether the steel pipe can be used as a steel pipe for X80-grade linepipes with required critical strain $\epsilon_{req}$=0.4% was also conducted.

In each case, appropriateness of the evaluation was inspected by FEM analysis.

TABLE 3

| No. | $\epsilon_y$ (%) | $\epsilon_H$ (%) | m |
|---|---|---|---|
| Q-1 | 0.17 | 0.17 | 0.015 |
| Q-2 | 0.24 | 0.24 | 0.021 |
| Q-3 | 0.28 | 0.28 | 0.025 |
| Q-4 | 0.25 | 0.7 | 0.014 |
| Q-5 | 0.27 | 1.0 | 0.014 |
| Q-6 | 0.27 | 1.0 | 0.006 |
| Q-7 | 0.27 | 1.0 | 0.007 |
| Q-8 | 0.31 | 1.2 | 0.008 |
| Q-9 | 0.27 | 1.5 | 0.007 |
| Q-10 | 0.31 | 2.0 | 0.007 |

As shown in Table 3, the yield strain $\epsilon_y$ of the stress-strain curve is 0.17 to 0.31% and the starting strain of strain-hardening $\epsilon_H$ is 0.17 to 2.0%. The modulus of modulus of strain-hardening mE is 0.006, 0.025. (D/t)$_{max}$ shown in the table is the value obtained by substituting these values in Equation (12).

Figure 21:
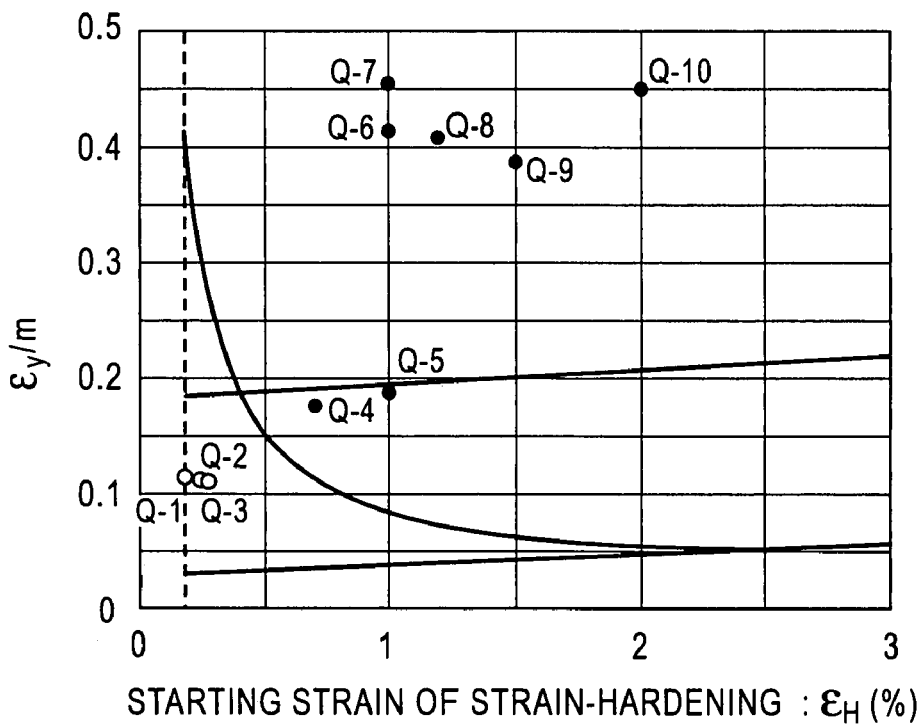
FIG. 21 is a graph showing a region related to a method for evaluating local buckling performance according to the fifth embodiment of the present invention.

FIG. 21 shows a region formed by the three equations described above in a coordinate plane with the ordinate indicating $\epsilon_y/m$ and the abscissa indicating $\epsilon_H$ while D=762.0 mm, t=15.6 mm, $\epsilon_{req}$=0.5%, and $\epsilon_y$ shown in Table 3 are substituted in Equations (30) and (31) above expressing the method for evaluating local buckling performance of a yield plateau model. In FIG. 21, coordinate points ($\epsilon_y/m$, $\epsilon_H$) of ten types of materials shown in Table 3 are respectively plotted.

In FIG. 21, Q-1, Q-2, and Q-3 are plotted in the solution region (region of PASS) and Q-4 to Q-10 are plotted outside the solution region (region of FAIL).

Figure 22:
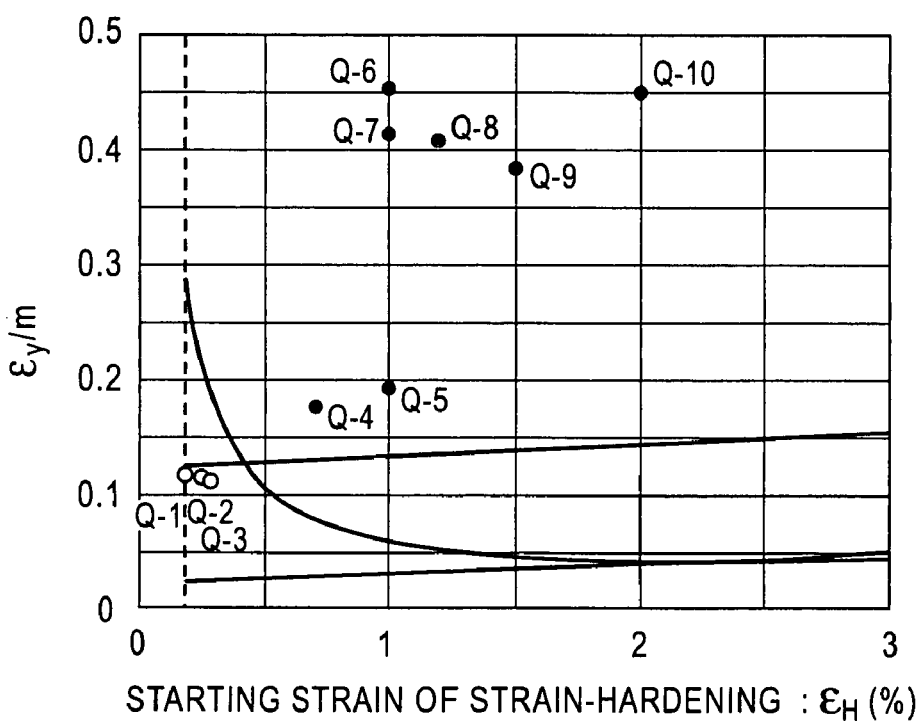
FIG. 22 is a graph showing a region related to a method for evaluating local buckling performance according to the fifth embodiment of the present invention.

FIG. 22 shows a region formed by the three equations described above in a coordinate plane with the ordinate indicating $\epsilon_y/m$ and the abscissa indicating $\epsilon_H$ while D=914.4 mm, t=15.2 mm, $\epsilon_{req}$=0.4%, and $\epsilon_y$ shown in Table 3 are substituted in Equations (30) and (31) above expressing the method for evaluating local buckling performance of a yield plateau model. In FIG. 22, coordinate points ($\epsilon_y/m$, $\epsilon_H$) of ten types of materials shown in Table 3 are respectively plotted.

In FIG. 22, Q-1, Q-2, and Q-3 are plotted in the solution region (region of PASS) and Q-4 to Q-10 are plotted outside the solution region (region of FAIL) as in the case of steel pipes with D=762.0 mm.

Next, whether the evaluation was appropriate was inspected by FEM analysis.

Table 4 shows compressive critical strains determined by FEM analysis for steel pipes with D=762.0 mm and D mm. The compressive critical strain of the steel pipe with D=762.0 mm is 0.28 to 0.63%, and that of the steel pipe with D=914.4 mm is 0.28 to 0.50%.

TABLE 4

| | Compressive critical strain (%) | |
|---|---|---|
| No. | Outer dia: 762.0 mm Thickness: 15.6 mm | Outer dia: 914.4 mm Thickness: 15.2 mm |
| Q-1 | 0.60 | 0.42 |
| Q-2 | 0.60 | 0.44 |
| Q-3 | 0.63 | 0.50 |
| Q-4 | 0.40 | 0.37 |
| Q-5 | 0.36 | 0.35 |
| Q-6 | 0.37 | 0.36 |
| Q-7 | 0.41 | 0.40 |
| Q-8 | 0.40 | 0.39 |
| Q-9 | 0.28 | 0.28 |
| Q-10 | 0.36 | 0.36 |

The results of comparative investigations of the results of evaluation based on the diagrams of FIGS. 21 and 22 and the solutions by FEM are shown in Tables 5 and 6. The compressive critical strains shown in Tables 5 and 6 are transcribed from Table 4.

TABLE 5

(Cases of steel pipes with D = 762.0 mm, t = 15.6 mm, and D/t = 48.8)

| Case | $\epsilon_y$ | m | $\epsilon_H$ | (D/t)max | $\epsilon$ cr (%) | Evaluation |
|---|---|---|---|---|---|---|
| Q-1 | 0.0017 | 0.015 | 0.0017 | 94.0 | 0.60 | PASS |
| Q-2 | 0.0024 | 0.021 | 0.0024 | 80.7 | 0.60 | PASS |
| Q-3 | 0.0028 | 0.025 | 0.0028 | 76.0 | 0.63 | PASS |
| Q-4 | 0.0025 | 0.014 | 0.0070 | 38.8 | 0.40 | FAIL |
| Q-5 | 0.0027 | 0.014 | 0.0100 | 31.3 | 0.36 | FAIL |
| Q-6 | 0.0027 | 0.006 | 0.0100 | 20.0 | 0.37 | FAIL |
| Q-7 | 0.0027 | 0.007 | 0.0100 | 20.9 | 0.41 | FAIL |
| Q-8 | 0.0031 | 0.008 | 0.0120 | 19.3 | 0.40 | FAIL |
| Q-9 | 0.0027 | 0.007 | 0.0150 | 17.9 | 0.28 | FAIL |
| Q-10 | 0.0031 | 0.007 | 0.0200 | 14.4 | 0.36 | FAIL |

TABLE 6

(Cases of steel pipes with D = 914.4 mm, t = 15.2 mm, and D/t = 60)

| Case | $\epsilon_y$ | m | $\epsilon_H$ | (D/t)max | $\epsilon$ cr (%) | Evaluation |
|---|---|---|---|---|---|---|
| Q-1 | 0.0017 | 0.015 | 0.0017 | 94.0 | 0.42 | PASS |
| Q-2 | 0.0024 | 0.021 | 0.0024 | 80.7 | 0.44 | PASS |
| Q-3 | 0.0028 | 0.025 | 0.0028 | 76.0 | 0.50 | PASS |
| Q-4 | 0.0025 | 0.014 | 0.0070 | 38.8 | 0.37 | FAIL |
| Q-5 | 0.0027 | 0.014 | 0.0100 | 31.3 | 0.35 | FAIL |
| Q-6 | 0.0027 | 0.006 | 0.0100 | 20.0 | 0.36 | FAIL |
| Q-7 | 0.0027 | 0.007 | 0.0100 | 20.9 | 0.40 | FAIL |
| Q-8 | 0.0031 | 0.008 | 0.0120 | 19.3 | 0.39 | FAIL |
| Q-9 | 0.0027 | 0.007 | 0.0150 | 17.9 | 0.28 | FAIL |
| Q-10 | 0.0031 | 0.007 | 0.0200 | 14.4 | 0.36 | FAIL |

Table 5 shows that when the required critical strain of the steel pipe with D=762.0 mm is set to 0.5%, Q-1 to Q-3 will pass and other materials will fail.

Table 6 shows that when the required critical strain of the steel pipe with D=914.4 mm is set to 0.4%, Q-1 to Q-3 will pass and other materials will fail.

In any case, the results of evaluation based on the diagrams shown in FIGS. 21 and 22 are consistent with the results by FEM, which proves the effectiveness of the present invention.

Note that the description above explains specific examples of methods for evaluating local buckling performance of a steel pipe by determining whether the yield strain $\epsilon_y$, the modulus of strain-hardening m, and the starting strain of strain-hardening $\epsilon_H$ of a steel pipe material obtained are within a particular region defined by Equations (30) and (31) above in a coordinate plane with the ordinate indicating $\epsilon_y/m$ and the abscissa indicating $\epsilon_H$.

However, the idea explained here is applicable not only to the method for evaluating local buckling performance but also to a method for designing a material for a steel pipe provided that the pipe diameter D, the pipe thickness t, and the required critical strain $\epsilon_{req}$ are given. In other words, in designing the material of the steel pipe provided that the pipe diameter D, the pipe thickness t, and the required critical strain $\epsilon_{req}$ are given, the yield strain $\epsilon_y$, the modulus of strain-hardening m, and the starting strain of strain-hardening $\epsilon_H$ should be determined such that the yield strain $\epsilon_y$, the modulus of strain-hardening m, and the starting strain of strain-hardening $\epsilon_H$ are in the above-described particular region in a coordinate plane with the ordinate indicating $\epsilon_y/m$ and the abscissa indicating $\epsilon_H$.

To be more specific, in designing the material of the steel pipe that satisfies D=762.0 mm, t=15.24 mm, and $\epsilon_{req}$=0.5%, these values are substituted in Equations (30) and (31) above, and the region defined by Equations (30) and (31) is drawn in a coordinate plane with the ordinate indicating $\epsilon_y/m$ and the abscissa indicating $\epsilon_H$ as in FIG. 20. Then the yield strain $\epsilon_y$, the modulus of strain-hardening m, and the starting strain of strain-hardening $\epsilon_H$ are determined such that they are in the solution region indicated in FIG. 20. A material having such modulus of strain-hardening m and starting strain of strain-hardening $\epsilon_H$ will satisfy D=762.0 mm, t=15.24 mm, and $\epsilon_{req}$=0.5%. In this manner, the quality that the material of the steel pipe should satisfy, i.e., the stress-strain relationship, can be easily determined, and efficient designing is possible.

Note that although compressive critical strain is used in the description above, since the compressive critical strain and the flexural critical strain have a quantitative relationship of about 1:2, the idea of the present invention can also be applied to flexural critical strain using this quantitative relationship.

EXAMPLES

A plurality of evaluation subjects were evaluated by the evaluation method of the second embodiment by setting D/t=50 and required critical strain $\epsilon_{req}$=1.5% as in the second embodiment. The results are shown in Table 7. The starting strain of strain-hardening $\epsilon_H$ of the materials to be evaluated were three, i.e., 1.5, 1.0, and 0.5. The materials with modulus of strain-hardening m=0.01, 0.02, 0.03, 0.04, and 0.05 were evaluated for each starting strain of strain-hardening $\epsilon_H$.

TABLE 7

| | | | | | Location of buckling region | Evaluation of required performance | |
| | | | | | | | |
| No. | $\epsilon$ y (%) | $\epsilon_H$ (%) | m | (D/t) cr | Buckling region | $\epsilon$ cr (%) | Evaluation results |
|---|---|---|---|---|---|---|---|
| 1-1 | 0.22 | 1.5 | 0.01 | 24.0 | Yield Plateau | — | FAIL |
| 1-2 | 0.22 | 1.5 | 0.02 | 35.3 | Yield Plateau | — | FAIL |
| 1-3 | 0.22 | 1.5 | 0.03 | 45.1 | Yield Plateau | — | FAIL |
| 1-4 | 0.22 | 1.5 | 0.04 | 54.4 | SH region | 1.78 | PASS |
| 1-5 | 0.22 | 1.5 | 0.05 | 63.9 | SH region | 2.45 | PASS |
| 2-1 | 0.22 | 1.0 | 0.01 | 29.1 | Yield Plateau | — | FAIL |
| 2-2 | 0.22 | 1.0 | 0.02 | 42.2 | Yield Plateau | — | FAIL |
| 2-3 | 0.22 | 1.0 | 0.03 | 53.0 | SH region | 1.12 | FAIL |
| 2-4 | 0.22 | 1.0 | 0.04 | 62.9 | SH region | 1.58 | PASS |
| 2-5 | 0.22 | 1.0 | 0.05 | 72.3 | SH region | 2.09 | PASS |
| 3-1 | 0.22 | 0.5 | 0.01 | 40.7 | Yield Plateau | — | FAIL |
| 3-2 | 0.22 | 0.5 | 0.02 | 58.2 | SH region | 0.68 | FAIL |
| 3-3 | 0.22 | 0.5 | 0.03 | 72.1 | SH region | 1.04 | FAIL |
| 3-4 | 0.22 | 0.5 | 0.04 | 84.3 | SH region | 1.42 | FAIL |
| 3-5 | 0.22 | 0.5 | 0.05 | 95.5 | SH region | 1.82 | PASS |

SH region: strain-hardening region

Samples 1-1 to 1-3 of the first group ($\delta_H$=1.5%) in Table 7 will undergo local buckling in the yield plateau region at D/t=50 since $(D/t)_{cr}$ is not larger than 50. Thus, the critical strain of samples 1-1 to 1-3 are presumed to be about the value of yield strain (0.22) and can be evaluated as FAIL without determining actual local buckling.

On the other hand, it can be understood that samples 1-4 and 1-5 have a (D/t), not less than 50 and undergo local buckling in the strain-hardening region. Since the critical strain $\epsilon_{cr}$ of 1-4 (which is shown in the second embodiment) is 1.78, which is larger than required critical strain $\epsilon_{req}$=1.5%, the samples are evaluated as PASS. The same applies to sample 1-5, which is also PASS.

The second group, 2-1 to 2-5 ($\epsilon_H$=1.0%), and the third group, 3-1 to 3.5 ($\epsilon_H$=0.5%) can be evaluated in the same manner, as shown in Table 7.

A portion of Table 7 is extracted to determine the relationship between the starting strain of strain-hardening $\epsilon_H$ and $(D/t)_{cr}$, which is shown in Table 8.

TABLE 8

| | | | | | Location of buckling region | Evaluation of required performance | |
| | | | | | | | |
| No. | $\epsilon$ y (%) | $\epsilon_H$ (%) | m | (D/t) cr | Buckling region | $\epsilon$ cr (%) | Evaluation results |
|---|---|---|---|---|---|---|---|
| 1-1 | 0.22 | 1.5 | 0.01 | 24.0 | Yield Plateau | — | FAIL |
| 1-2 | 0.22 | 1.5 | 0.02 | 35.3 | Yield Plateau | — | FAIL |
| 1-4 | 0.22 | 1.5 | 0.04 | 54.4 | SH region | 1.78 | PASS |
| 2-1 | 0.22 | 1.0 | 0.01 | 29.1 | Yield Plateau | — | FAIL |
| 2-2 | 0.22 | 1.0 | 0.02 | 42.2 | Yield Plateau | — | FAIL |
| 2-4 | 0.22 | 1.0 | 0.04 | 62.9 | SH region | 1.58 | PASS |
| 3-1 | 0.22 | 0.5 | 0.01 | 40.7 | Yield Plateau | — | FAIL |
| 3-2 | 0.22 | 0.5 | 0.02 | 58.2 | SH region | 0.68 | FAIL |
| 3-4 | 0.22 | 0.5 | 0.04 | 84.3 | SH region | 1.42 | FAIL |

SH: strain-hardening region

Figure 8:
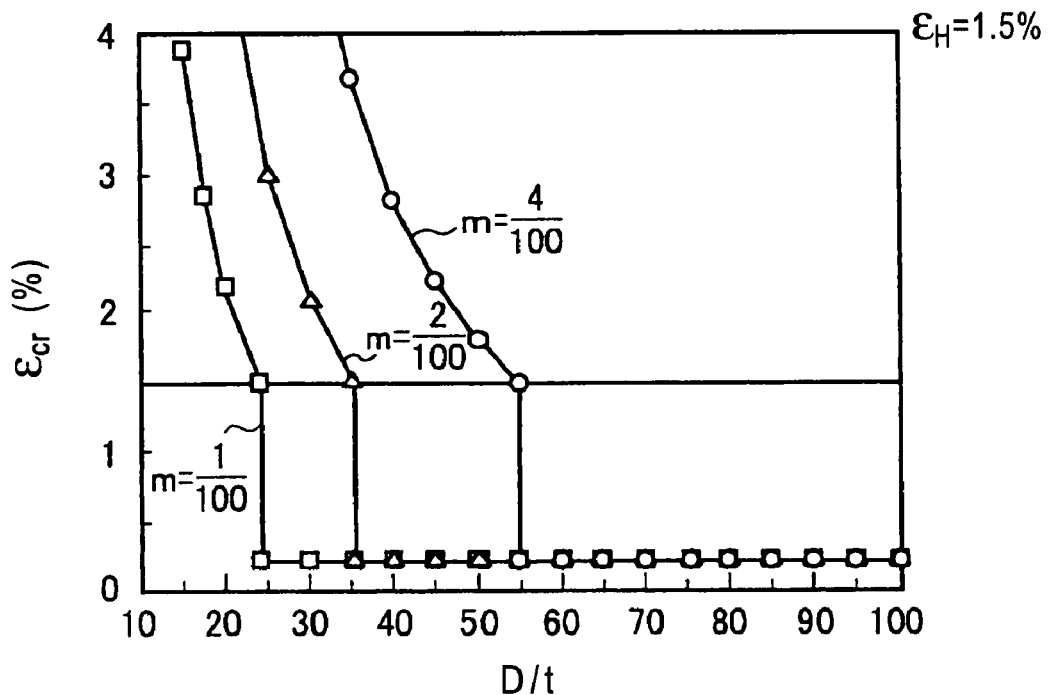
FIG. 8 is a graph showing the relationship between critical strain and D/t of a subject to be evaluated according to an example (No. 1).
Figure 9:
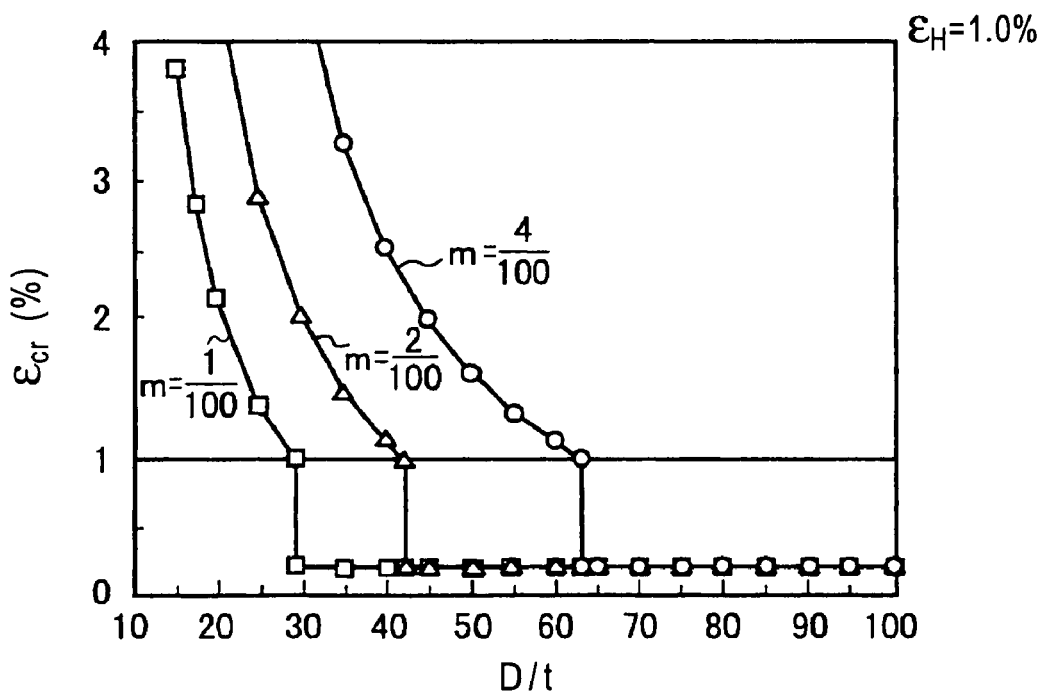
FIG. 9 is a graph showing the relationship between critical strain and D/t of a subject to be evaluated according to an example (No. 2).
Figure 10:
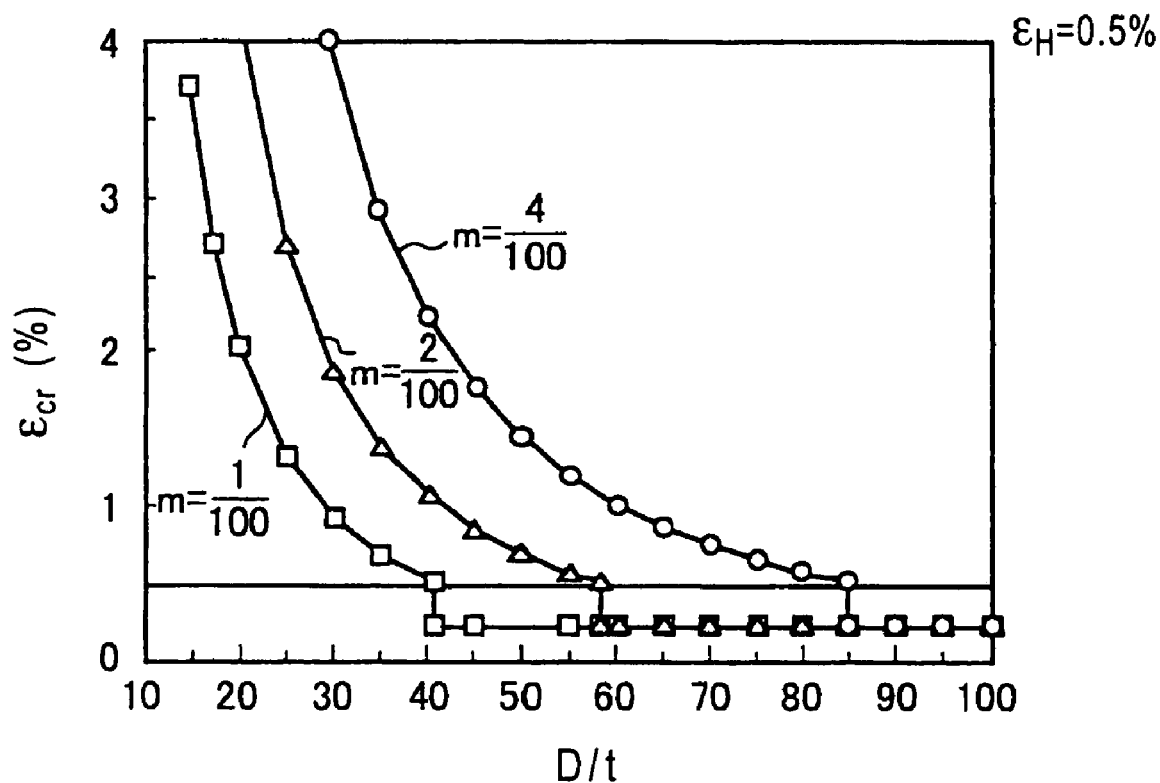
FIG. 10 is a graph showing the relationship between critical strain and D/t of a subject to be evaluated according to an example (No. 3).

The relationship between the critical strain $\epsilon_{cr}$ of the evaluation samples shown in Table 8 and D/t was plotted with the ordinate indicating the critical strain $\epsilon_{cr}$ and the abscissa indicating D/t for every group, and is shown in FIGS. 8 to 10.

Figure 11:
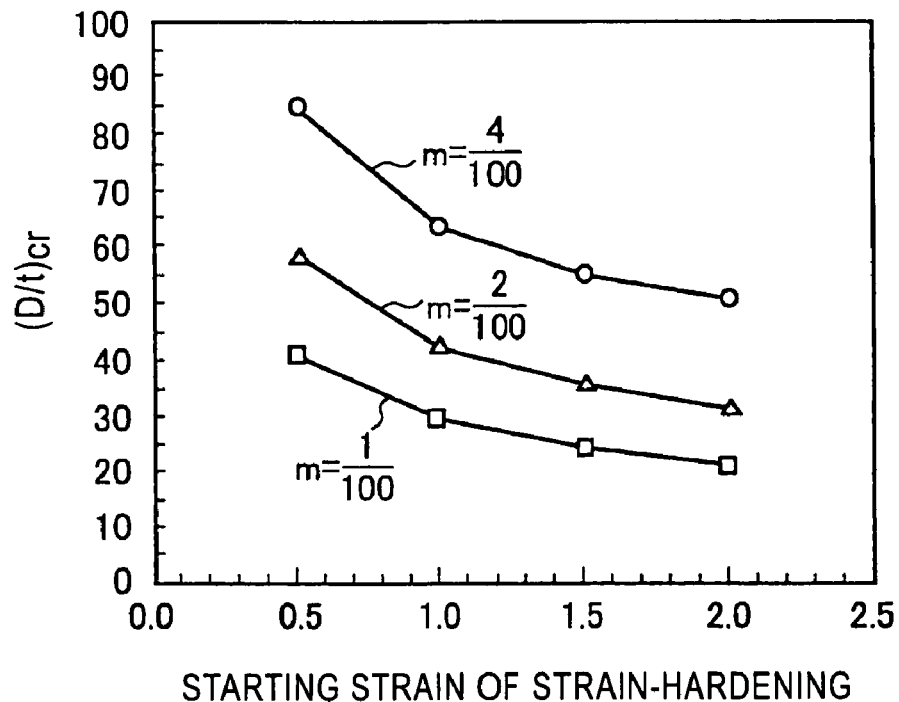
FIG. 11 is a graph showing the relationship between (D/t) cr and the starting strain of strain-hardening of a subject to be evaluated according to an example of the present invention.
Figure 12:
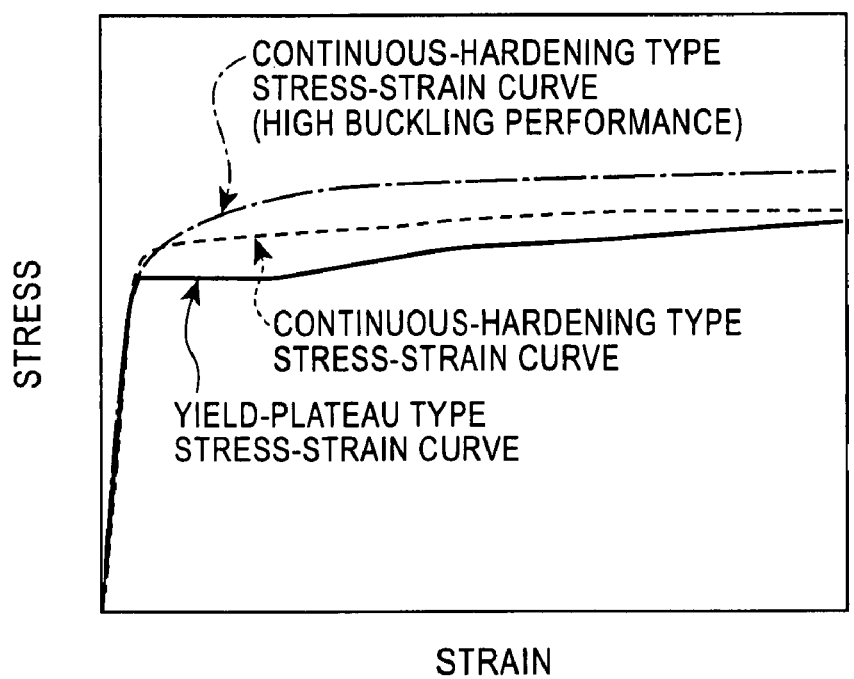
FIG. 12 is a graph for explaining stress-strain curves of steel materials.
Figure 13:
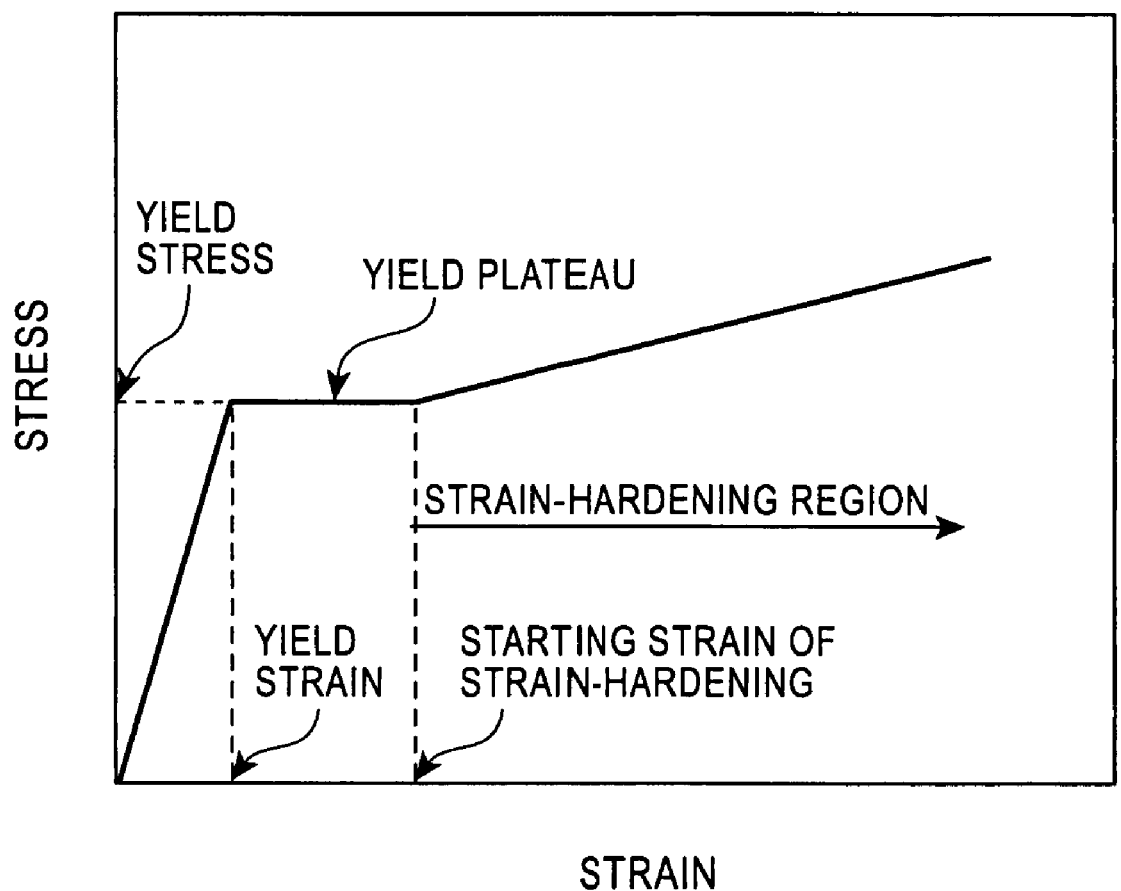
FIG. 13 is a graph for explaining a stress-strain curve of a yield plateau-type steel material.
Figure 14:
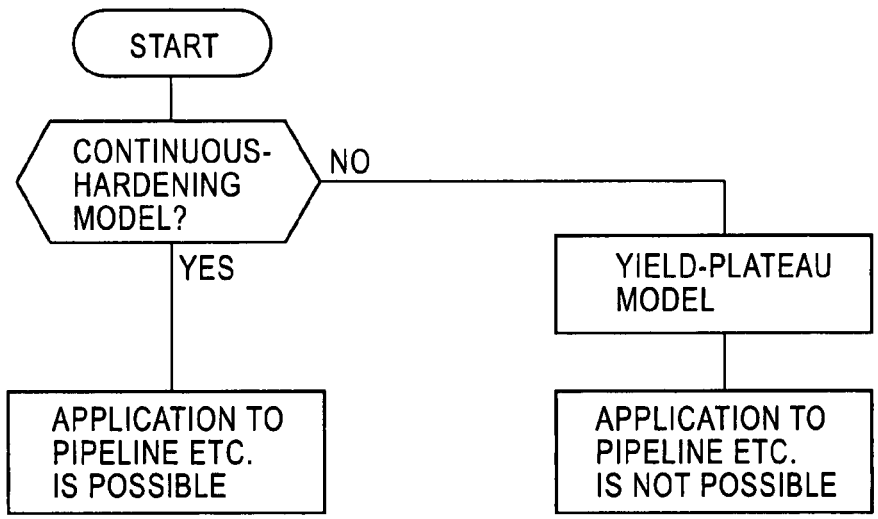
FIG. 14 is a diagram for explaining the idea of the present invention.
Figure 14:
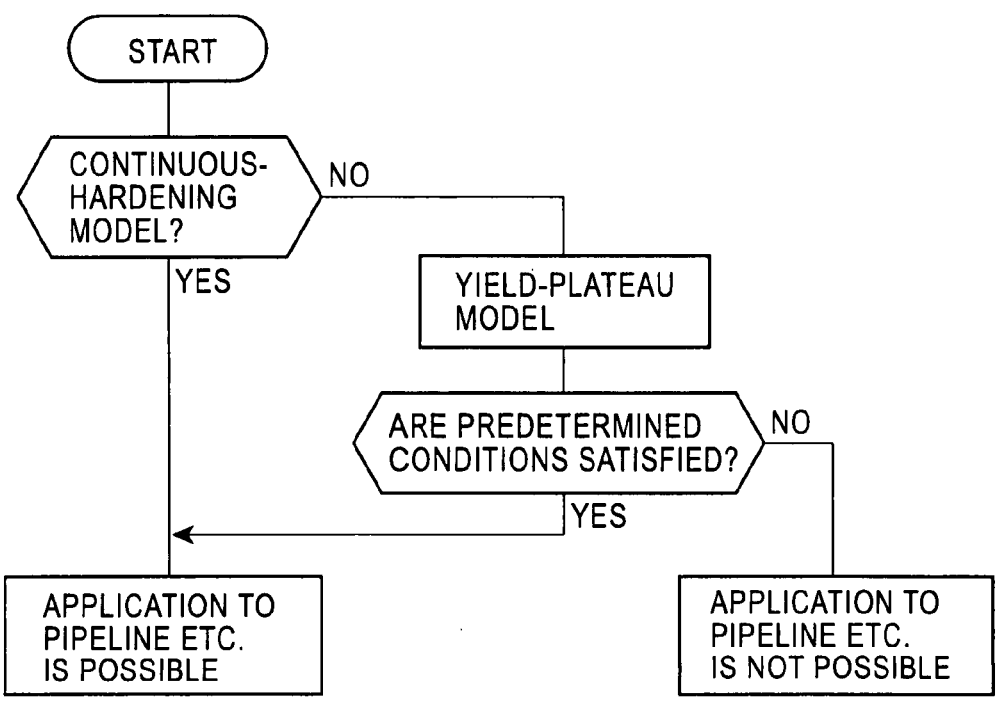
Figure 15:
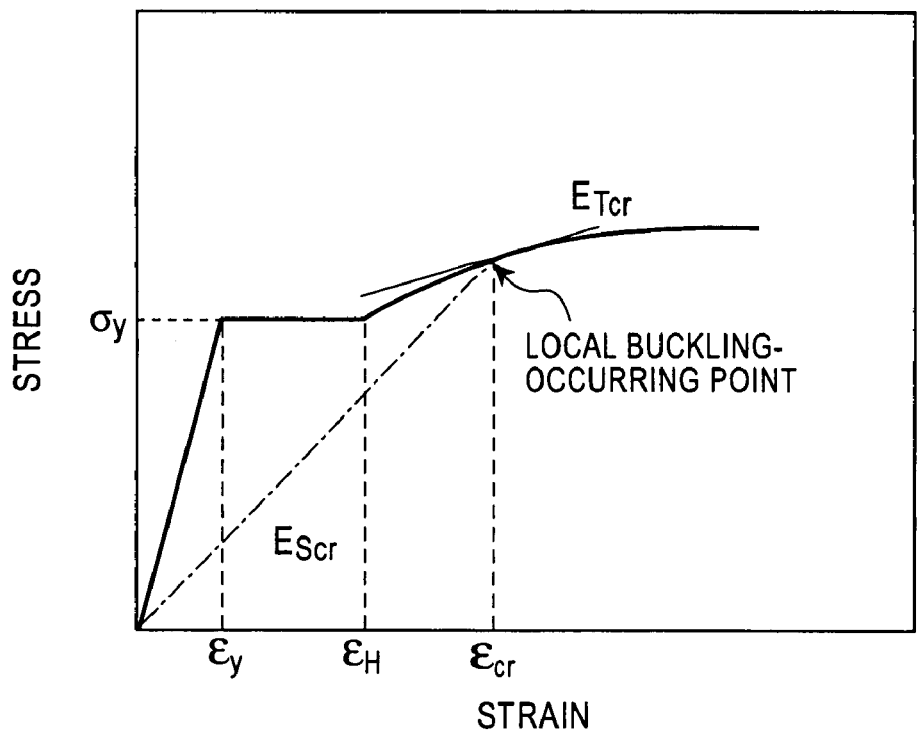
FIG. 15 is a graph for explaining a stress-strain curve of a steel pipe formed of a yield plateau-type steel material.
Figure 16:
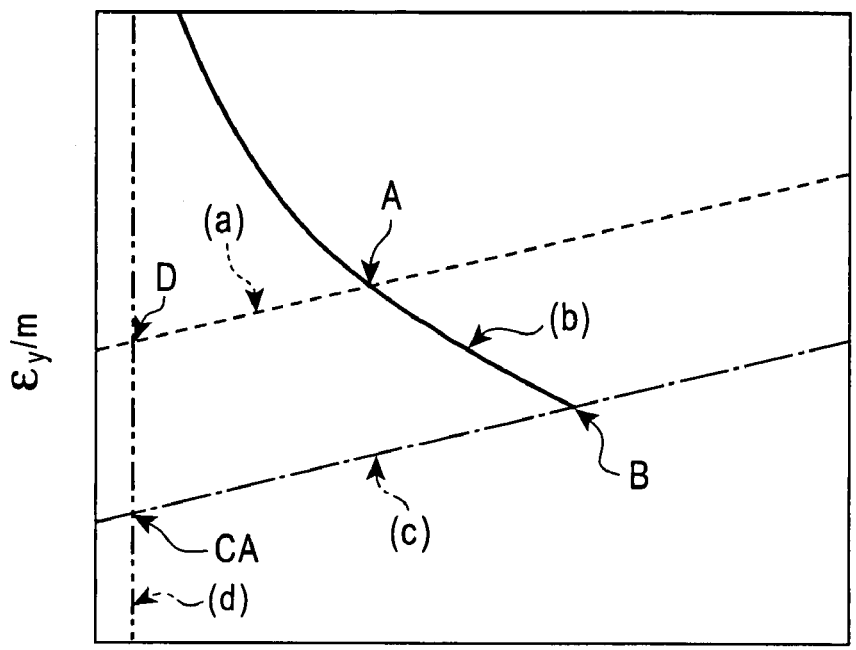
FIG. 16 is a graph showing a region related to a method for evaluating local buckling performance of the present invention.

FIG. 11 shows a graph with the ordinate indicating $(D/t)_{cr}$ and the abscissa indicating the starting strain of strain-hardening.

As is apparent from FIGS. 8 to 10 or FIG. 11, $(D/t)_{cr}$ increases as the starting strain of strain-hardening decreases, i.e., as the yield plateau shortens, irrespective of the modulus of strain-hardening m. In other words, this shows that a steel pipe will undergo local buckling in the strain-hardening region, i.e., will exhibit excellent buckling performance, even when the thickness is small as the starting strain of strain-hardening decreases (as the yield plateau shortens).

Irrespective of the value of the strain-hardening region-starting strain (length of the yield plateau), $(D/t)_{cr}$ increases as the modulus of strain-hardening m increases. In other words, this shows that a steel pipe will undergo local buckling in the strain-hardening region, i.e., will exhibit excellent buckling performance, even when the thickness is small as the modulus of strain-hardening m increases.

Industrial Applicability

According to a method for evaluating local buckling performance of a steel pipe of the present invention, the usage of the steel pipe can be easily identified since the appropriateness of the buckling performance of the steel pipe can be easily evaluated.

According to a method for designing a steel pipe of the present invention, even a material having a yield plateau can be treated as if it is a continuous hardening-type material since the pipe diameter/pipe thickness ratio (D/t) of the steel pipe to be designed is determined by determining the pipe diameter/pipe thickness ratio $(D/t)_{cr}$ at which the critical strain of the steel pipe having a stress-strain relationship becomes the same as the starting strain of strain-hardening in the stress-strain relationship and then determining the pipe diameter/pipe thickness ratio (D/t) of the steel pipe to be evaluated while maintaining the pipe diameter/pipe thickness ratio (D/t) of the steel pipe to be evaluated to be smaller than the pipe diameter/pipe thickness ratio $(D/t)_{cr}$.

The invention claimed is:

1. A method for evaluating local buckling performance of a steel pipe, wherein the pipe diameter D, the pipe thickness t, and the required critical strain $\epsilon_{req}$ are known, characterized in obtaining a stress-strain relationship of a material having a yield plateau in the stress-strain relationship; determining whether the yield strain $\epsilon_y$, the modulus of strain-hardening m, and the starting strain of strain-hardening $\epsilon_H$ of a stress-strain curve of the stress-strain relationship obtained are in a region defined by equations below in a coordinate plane with an ordinate indicating $\epsilon_y/m$ and an abscissa indicating $\epsilon_H$; and evaluating that the steel pipe has a possibility of being applied to a structure that requires plastic design when these values are within the region and that the steel pipe has no possibility of being applied to a structure that requires plastic design when these values are outside the region:

$$\left\{\epsilon_H + \frac{4}{3}\left(\frac{t}{D}\right)\right\} \le \frac{\epsilon_y}{m} \le \left\{\epsilon_H + \frac{16}{9\epsilon_{req}}\left(\frac{t}{D}\right)^2\right\} \quad (30)$$

wherein $\epsilon_y \le \epsilon_H \le \epsilon_{req}$ and $$\left\{\epsilon_H + \frac{4}{3}\left(\frac{t}{D}\right)\right\} \le \frac{\epsilon_y}{m} \le \left\{\epsilon_H + \frac{16}{9\epsilon_H}\left(\frac{t}{D}\right)^2\right\} \quad (31)$$

wherein $$\epsilon_{req} < \epsilon_H < \frac{4}{3}\left(\frac{t}{D}\right).$$

2. A method for designing a material for a steel pipe, wherein a pipe diameter D, a pipe thickness t, and a required critical strain $\epsilon_{req}$ are known, characterized in that, in determining a stress-strain relationship of a material having a yield plateau in the stress-strain relationship, the yield strain $\epsilon_y$, the modulus of strain-hardening m, and the starting strain of strain-hardening $\epsilon_H$ of a stress-strain curve of the obtained stress-strain relationship are determined such that the yield strain $\epsilon_y$, the modulus of strain-hardening m, and the starting strain of strain-hardening $\epsilon_H$ of a material to be designed are in a range defined by equations below in a coordinate plane with an ordinate indicating $\epsilon_y/m$ and an abscissa indicating $\epsilon_H$:

$$\left\{\epsilon_H + \frac{4}{3}\left(\frac{t}{D}\right)\right\} \le \frac{\epsilon_y}{m} \le \left\{\epsilon_H + \frac{16}{9\epsilon_{req}}\left(\frac{t}{D}\right)^2\right\} \quad (30)$$

wherein $\epsilon_y \le \epsilon_H \le \epsilon_{req}$ and $$\left\{\epsilon_H + \frac{4}{3}\left(\frac{t}{D}\right)\right\} \le \frac{\epsilon_y}{m} \le \left\{\epsilon_H + \frac{16}{9\epsilon_H}\left(\frac{t}{D}\right)^2\right\} \quad (31)$$

wherein $$\epsilon_{req} < \epsilon_H < \frac{4}{3}\left(\frac{t}{D}\right).$$

3. A steel pipe, material of which is designed by the method for designing the material of the steel pipe according to claim 2.

4. A steel pipe evaluated as being applicable to a structure that requires plastic design by the method for evaluating local buckling performance of the steel pipe according to claim 2.

* * * * *